(12) United States Patent
Kless

(10) Patent No.: US 7,794,984 B2
(45) Date of Patent: *Sep. 14, 2010

(54) TEMPLATE-DEPENDENT NUCLEIC ACID POLYMERIZATION USING OLIGONUCLEOTIDE TRIPHOSPHATES BUILDING BLOCKS

(75) Inventor: Hadar Kless, Rechovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 272 days.

This patent is subject to a terminal disclaimer.

(21) Appl. No.: 12/003,476

(22) Filed: Dec. 26, 2007

(65) Prior Publication Data

US 2010/0028954 A1 Feb. 4, 2010

Related U.S. Application Data

(60) Continuation of application No. 11/211,444, filed on Aug. 26, 2005, now abandoned, which is a division of application No. 10/069,236, filed as application No. PCT/IL00/00515 on Aug. 29, 2000, now Pat. No. 7,060,440, which is a continuation of application No. 09/387,777, filed on Sep. 1, 1999.

(51) Int. Cl.
*C12P 19/34* (2006.01)
(52) U.S. Cl. .................................. 435/91.2; 435/91.21
(58) Field of Classification Search ........................ None
See application file for complete search history.

(56) References Cited

U.S. PATENT DOCUMENTS

| 5,436,143 A | 7/1995 | Hyman |
| 5,714,320 A | 2/1998 | Kool |
| 7,060,440 B1 * | 6/2006 | Kless .............................. 435/6 |
| 2005/0287592 A1 | 12/2005 | Kless |

FOREIGN PATENT DOCUMENTS

| WO | WO 98/23733 | 6/1998 |
| WO | WO 01/16366 | 3/2001 |

OTHER PUBLICATIONS

Benner et al. "Redesigning Nucleuc Acids", Pure & Applied Chemistry, 70(2): 263-266, 1998.
Carola et al. "Nucleic Acid Enzymes", Current Opinion in Chemical Biology, 3:274-283, 1999.
Hanaki et al. "Two Different Reactions Involved in the Primer/Template-Independent Polymerization of dATP and dTTP by Taq DNA Polymerase", Biochemistry and Biophysics Research Communications, 244(1): 210-209, 1998. Abstract.
Herkowitz "Functional Inactivation of Genes by Dominant Negative Mutations", Nature, 329: 219-222, Sep. 17, 1987.
Jahnke et al. "Dinucleotides Incorporating Isomeric Nucleosides: Synthesis, Structural and Stereochemical Characterization, and Enzymology", Nucleosides & Nucleotides, 16(7-9): 1087-1090, 1997.
Kayushin et al. "A Convenient Approach to the Synthesis of Trinucleotide Phosphoramidites-Synthons for the Generation of Oligonucleotide/Peptide Libraries", Nucleic Acids Research, 24(19): 3748-3755, 1996.
Kool "Replication of Non-Hydrogen Bonded Bases by DNA Polymerases: A Mechanism for Steric Matching", Biopolymers (Nucleic Acid Sciences), 48: 3-17, 1988.
Koppitz et al. "Formation of Oligonucleotide-PNA-Chimeras by Template-Directed Ligation", Journal of the American Chemical Society, 120:4563-4569, 1998. Abstract.
Landegren et al. "A Ligase-Mediated Gene Detection Technique", Science, 241: 1077-1080, 1991.
Li et al. "Crystal Structures of Open and Closed Forms of Binary and Ternary Complexes if the Large Fragment of Thermus Aquaticus DNA Polymerase 1: Structural Basis for Nucleotide Incorporation", The EMBO Journal, 17(24):7514-7525, 1998.
Lutz et al. "An In Vitro Screening Technique for DNA Polymerases That Can Incorporate Modified Nucleotides. Pseudothymidine as A Substrate for Thermostable Polymerases", Nucleic Acids Research, 27(13): 2792-2798, 1999.
Moroney et al. "Abortive Products as Initiating Nucleotides During Transciption by T7 RNA Polymerase", Biochemistry, 30(42): 10343-10349, 1991.
Ordoukhanian et al. "Solid Phase-Supported Thymine Dimers for the Construction of Dimer-Containing DNA by Combined Chemical and Enzymatic Synthesis: A Potentially General Method for the Efficient Incorporation of Modified Nucleotides into DNA", Nucleic Acids Res., 25(19): 3783-3786, 1977.
Schmidt et al. "Information Transfer from DNA to Peptide Nucleic Acids by Template-Directed Syntheses", Nucleic Acids Research, 25(23): 4792-4796, 1997.
Office Action Dated Apr. 29, 2007 From the Israeli Patent Office Re.: Application No. 148344.
Official Action Dated Nov. 1, 2006 From the US Patent and Trademark Office Re.: U.S. Appl. No. 11/211,444.

*Primary Examiner*—Gary Benzion
*Assistant Examiner*—Cynthia B Wilder

(57) ABSTRACT

A novel use of a template-dependent polymerase. The novel use is effected by employing the template-dependent polymerase for incorporating at least one oligonucleotide triphosphate onto a nascent oligonucleotide-3'-OH in a template-dependent manner.

4 Claims, 7 Drawing Sheets

2'-deoxyguanosine    2'-deoxycytidine

2'-deoxyadenosine    2'-deoxythimidine

2'-deoxynucleoside

I. Primer extension

+dG, dA, dC & TpT3p        +dG, dA & dC

II. Exo VII

III. PCR

A:
TC GA TT GC TA AG TC CG AT GA TA GC TG AT CG TT CG CT TA AA

B:
TC GA TT GC TA AG TC CG AT GA TA GC GG AT CG TT CG CT TA AA

Dinucleotide sets:
set I:   AA, AC, AG, AT, CG, CT, GA, GC, TA, TC and TT
set II:  same, but with CC instead of AC.

SEQUENCE LISTING

<160> NUMBER OF SEQ ID NOS: 100

<210> SEQ ID NO 1
<211> LENGTH: 2
<212> TYPE: DNA
<213> ORGANISM: Artificial sequence
<220> FEATURE:
<223> OTHER INFORMATION: synthetic oligonucleotide

<400> SEQUENCE: 1 aa                                                                    2

<210> SEQ ID NO 2
<211> LENGTH: 2
<212> TYPE: DNA
<213> ORGANISM: Artificial sequence
<220> FEATURE:
<223> OTHER INFORMATION: synthetic oligonucleotide

<400> SEQUENCE: 2 ac                                                                    2

<210> SEQ ID NO 3
<211> LENGTH: 2
<212> TYPE: DNA
<213> ORGANISM: Artificial sequence
<220> FEATURE:
<223> OTHER INFORMATION: synthetic oligonucleotide

<400> SEQUENCE: 3 ag                                                                    2

<210> SEQ ID NO 4
<211> LENGTH: 2
<212> TYPE: DNA
<213> ORGANISM: Artificial sequence
<220> FEATURE:
<223> OTHER INFORMATION: synthetic oligonucleotide

<400> SEQUENCE: 4 at                                                                    2

<210> SEQ ID NO 5
<211> LENGTH: 2
<212> TYPE: DNA
<213> ORGANISM: Artificial sequence
<220> FEATURE:
<223> OTHER INFORMATION: synthetic oligonucleotide

<400> SEQUENCE: 5 ca                                                                    2

<210> SEQ ID NO 6
<211> LENGTH: 2
<212> TYPE: DNA
<213> ORGANISM: Artificial sequence
<220> FEATURE:
<223> OTHER INFORMATION: synthetic oligonucleotide

<400> SEQUENCE: 6 cc                                                                    2

<210> SEQ ID NO 7
<211> LENGTH: 2

```
<212> TYPE: DNA
<213> ORGANISM: Artificial sequence
<220> FEATURE:
<223> OTHER INFORMATION: synthetic oligonucleotide

<400> SEQUENCE: 7 cg                                                                          2

<210> SEQ ID NO 8
<211> LENGTH: 2
<212> TYPE: DNA
<213> ORGANISM: Artificial sequence
<220> FEATURE:
<223> OTHER INFORMATION: synthetic oligonucleotide

<400> SEQUENCE: 8 ct                                                                          2

<210> SEQ ID NO 9
<211> LENGTH: 2
<212> TYPE: DNA
<213> ORGANISM: Artificial sequence
<220> FEATURE:
<223> OTHER INFORMATION: synthetic oligonucleotide

<400> SEQUENCE: 9 ga                                                                          2

<210> SEQ ID NO 10
<211> LENGTH: 2
<212> TYPE: DNA
<213> ORGANISM: Artificial sequence
<220> FEATURE:
<223> OTHER INFORMATION: synthetic oligonucleotide

<400> SEQUENCE: 10 gc                                                                          2

<210> SEQ ID NO 11
<211> LENGTH: 2
<212> TYPE: DNA
<213> ORGANISM: Artificial sequence
<220> FEATURE:
<223> OTHER INFORMATION: synthetic oligonucleotide

<400> SEQUENCE: 11 gg                                                                          2

<210> SEQ ID NO 12
<211> LENGTH: 2
<212> TYPE: DNA
<213> ORGANISM: Artificial sequence
<220> FEATURE:
<223> OTHER INFORMATION: synthetic oligonucleotide

<400> SEQUENCE: 12 gt                                                                          2

<210> SEQ ID NO 13
<211> LENGTH: 2
<212> TYPE: DNA
<213> ORGANISM: Artificial sequence
<220> FEATURE:
<223> OTHER INFORMATION: synthetic oligonucleotide

<400> SEQUENCE: 13
```

-continued ta                                                                                              2

<210> SEQ ID NO 14
<211> LENGTH: 2
<212> TYPE: DNA
<213> ORGANISM: Artificial sequence
<220> FEATURE:
<223> OTHER INFORMATION: synthetic oligonucleotide

<400> SEQUENCE: 14 tc                                                                                              2

<210> SEQ ID NO 15
<211> LENGTH: 2
<212> TYPE: DNA
<213> ORGANISM: Artificial sequence
<220> FEATURE:
<223> OTHER INFORMATION: synthetic oligonucleotide

<400> SEQUENCE: 15 tg                                                                                              2

<210> SEQ ID NO 16
<211> LENGTH: 2
<212> TYPE: DNA
<213> ORGANISM: Artificial sequence
<220> FEATURE:
<223> OTHER INFORMATION: synthetic oligonucleotide

<400> SEQUENCE: 16 tt                                                                                              2

<210> SEQ ID NO 17
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 17 aaa                                                                                             3

<210> SEQ ID NO 18
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 18 aac                                                                                             3

<210> SEQ ID NO 19
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 19 aag                                                                                             3

<210> SEQ ID NO 20
<211> LENGTH: 3
<212> TYPE: DNA
<213> ORGANISM: Artificial sequence

```
<220> FEATURE:
<223> OTHER INFORMATION: synthetic oligonucleotide

<400> SEQUENCE: 20 aat                                                                          3

<210> SEQ ID NO 21
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 21 aca                                                                          3

<210> SEQ ID NO 22
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 22 acc                                                                          3

<210> SEQ ID NO 23
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 23 acg                                                                          3

<210> SEQ ID NO 24
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 24 act                                                                          3

<210> SEQ ID NO 25
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 25 aga                                                                          3

<210> SEQ ID NO 26
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 26 agc                                                                          3
```

-continued

```
<210> SEQ ID NO 27
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 27 agg                                                                      3

<210> SEQ ID NO 28
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 28 agt                                                                      3

<210> SEQ ID NO 29
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 29 ata                                                                      3

<210> SEQ ID NO 30
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 30 atc                                                                      3

<210> SEQ ID NO 31
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 31 atg                                                                      3

<210> SEQ ID NO 32
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 32 att                                                                      3

<210> SEQ ID NO 33
<211> LENGTH: 3
<212> TYPE: DNA
<213> ORGANISM: Artificial sequence
<220> FEATURE:
<223> OTHER INFORMATION: synthetic oligonucleotide
```

<400> SEQUENCE: 33 caa                                                                     3

<210> SEQ ID NO 34
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 34 cac                                                                     3

<210> SEQ ID NO 35
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 35 cag                                                                     3

<210> SEQ ID NO 36
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 36 cat                                                                     3

<210> SEQ ID NO 37
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 37 cca                                                                     3

<210> SEQ ID NO 38
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 38 ccc                                                                     3

<210> SEQ ID NO 39
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 39 ccg                                                                     3

<210> SEQ ID NO 40

```
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 40 cct                                                                       3

<210> SEQ ID NO 41
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 41 cga                                                                       3

<210> SEQ ID NO 42
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 42 cgc                                                                       3

<210> SEQ ID NO 43
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 43 cgg                                                                       3

<210> SEQ ID NO 44
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 44 cgt                                                                       3

<210> SEQ ID NO 45
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 45 cta                                                                       3

<210> SEQ ID NO 46
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 46
```

-continued ctc                                                                3

<210> SEQ ID NO 47
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 47 ctg                                                                3

<210> SEQ ID NO 48
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 48 ctt                                                                3

<210> SEQ ID NO 49
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 49 gaa                                                                3

<210> SEQ ID NO 50
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 50 gac                                                                3

<210> SEQ ID NO 51
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 51 gag                                                                3

<210> SEQ ID NO 52
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 52 gat                                                                3

<210> SEQ ID NO 53
<211> LENGTH: 3
<212> TYPE: DNA

```
<213> ORGANISM: Artificial sequence
<220> FEATURE:
<223> OTHER INFORMATION: synthetic oligonucleotide

<400> SEQUENCE: 53 gca                                                                        3

<210> SEQ ID NO 54
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 54 gcc                                                                        3

<210> SEQ ID NO 55
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 55 gcg                                                                        3

<210> SEQ ID NO 56
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 56 gct                                                                        3

<210> SEQ ID NO 57
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 57 gga                                                                        3

<210> SEQ ID NO 58
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 58 ggc                                                                        3

<210> SEQ ID NO 59
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 59 ggg                                                                        3
```

```
<210> SEQ ID NO 60
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 60 ggt                                                                        3

<210> SEQ ID NO 61
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 61 gta                                                                        3

<210> SEQ ID NO 62
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 62 gtc                                                                        3

<210> SEQ ID NO 63
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 63 gtg                                                                        3

<210> SEQ ID NO 64
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 64 gtt                                                                        3

<210> SEQ ID NO 65
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 65 taa                                                                        3

<210> SEQ ID NO 66
<211> LENGTH: 3
<212> TYPE: DNA
<213> ORGANISM: Artificial sequence
<220> FEATURE:
```

<223> OTHER INFORMATION: synthetic oligonucleotide

<400> SEQUENCE: 66 tac                                                                 3

<210> SEQ ID NO 67
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 67 tag                                                                 3

<210> SEQ ID NO 68
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 68 tat                                                                 3

<210> SEQ ID NO 69
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 69 tca                                                                 3

<210> SEQ ID NO 70
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 70 tcc                                                                 3

<210> SEQ ID NO 71
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 71 tcg                                                                 3

<210> SEQ ID NO 72
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 72 tct                                                                 3

```
<210> SEQ ID NO 73
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 73 tga                                                                 3

<210> SEQ ID NO 74
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 74 tgc                                                                 3

<210> SEQ ID NO 75
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 75 tgg                                                                 3

<210> SEQ ID NO 76
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 76 tgt                                                                 3

<210> SEQ ID NO 77
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 77 tta                                                                 3

<210> SEQ ID NO 78
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 78 ttc                                                                 3

<210> SEQ ID NO 79
<211> LENGTH: 3
<212> TYPE: DNA
<213> ORGANISM: Artificial sequence
<220> FEATURE:
<223> OTHER INFORMATION: synthetic oligonucleotide
```

<400> SEQUENCE: 79 ttg                                                                 3

<210> SEQ ID NO 80
<211> LENGTH: 3
<212> TYPE: DNA
<213> ORGANISM: Artificial sequence
<220> FEATURE:
<223> OTHER INFORMATION: synthetic oligonucleotide

<400> SEQUENCE: 80 ttt                                                                 3

<210> SEQ ID NO 81
<211> LENGTH: 22
<212> TYPE: DNA
<213> ORGANISM: Artificial sequence
<220> FEATURE:
<223> OTHER INFORMATION: synthetic oligonucleotide

<400> SEQUENCE: 81
gtaatacgac tcactatagg gc                                           22

<210> SEQ ID NO 82
<211> LENGTH: 47
<212> TYPE: DNA
<213> ORGANISM: Artificial sequence
<220> FEATURE:
<223> OTHER INFORMATION: synthetic oligonucleotide

<400> SEQUENCE: 82
ggtgtccttt gcgtgtcgtg taaatgccct atagtgagtc gtattac                47

<210> SEQ ID NO 83
<211> LENGTH: 48
<212> TYPE: DNA
<213> ORGANISM: Artificial sequence
<220> FEATURE:
<223> OTHER INFORMATION: synthetic oligonucleotide

<400> SEQUENCE: 83
ggtgtccttt gcgtgtcgtg taaaatgccc tatagtgagt cgtattac               48

<210> SEQ ID NO 84
<211> LENGTH: 49
<212> TYPE: DNA
<213> ORGANISM: Artificial sequence
<220> FEATURE:
<223> OTHER INFORMATION: synthetic oligonucleotide

<400> SEQUENCE: 84
ggtgtccttt gcgtgtcgtg taaaaatgcc ctatagtgag tcgtattac              49

<210> SEQ ID NO 85
<211> LENGTH: 45
<212> TYPE: DNA
<213> ORGANISM: Artificial sequence
<220> FEATURE:
<223> OTHER INFORMATION: synthetic oligonucleotide

<400> SEQUENCE: 85
ggccgaagag ggtctccacg taccggtgtc ctttgcgtgt cgtgt                  45

<210> SEQ ID NO 86
<211> LENGTH: 17

<212> TYPE: DNA
<213> ORGANISM: Artificial sequence
<220> FEATURE:
<223> OTHER INFORMATION: synthetic oligonucleotide

<400> SEQUENCE: 86
ggccgaagag ggtctcc                                                    17

<210> SEQ ID NO 87
<211> LENGTH: 40
<212> TYPE: DNA
<213> ORGANISM: Artificial sequence
<220> FEATURE:
<223> OTHER INFORMATION: synthetic oligonucleotide

<400> SEQUENCE: 87
tcgattgcta agtccgatga tagctgatcg ttcgcttaaa                            40

<210> SEQ ID NO 88
<211> LENGTH: 40
<212> TYPE: DNA
<213> ORGANISM: Artificial sequence
<220> FEATURE:
<223> OTHER INFORMATION: synthetic oligonucleotide

<400> SEQUENCE: 88
tcgattgcta agtccgatga tagcggatcg ttcgcttaaa                            40

<210> SEQ ID NO 89
<211> LENGTH: 2
<212> TYPE: DNA
<213> ORGANISM: Artificial sequence
<220> FEATURE:
<223> OTHER INFORMATION: synthetic oligonucleotide

<400> SEQUENCE: 89 ca                                                                     2

<210> SEQ ID NO 90
<211> LENGTH: 2
<212> TYPE: DNA
<213> ORGANISM: Artificial sequence
<220> FEATURE:
<223> OTHER INFORMATION: synthetic oligonucleotide

<400> SEQUENCE: 90 cc                                                                     2

<210> SEQ ID NO 91
<211> LENGTH: 2
<212> TYPE: DNA
<213> ORGANISM: Artificial sequence
<220> FEATURE:
<223> OTHER INFORMATION: synthetic oligonucleotide

<400> SEQUENCE: 91 ag                                                                     2

<210> SEQ ID NO 92
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 92

-continued gtaatacgac tcactatagg                                                    20

<210> SEQ ID NO 93
<211> LENGTH: 32
<212> TYPE: DNA
<213> ORGANISM: Artificial sequence
<220> FEATURE:
<223> OTHER INFORMATION: synthetic oligonucleotide

<400> SEQUENCE: 93
aaaatgtgtg tgcctatagt gagtcgtatt ac                                      32

<210> SEQ ID NO 94
<211> LENGTH: 32
<212> TYPE: DNA
<213> ORGANISM: Artificial sequence
<220> FEATURE:
<223> OTHER INFORMATION: synthetic oligonucleotide

<400> SEQUENCE: 94
aatgaatgaa tgcctatagt gagtcgtatt ac                                      32

<210> SEQ ID NO 95
<211> LENGTH: 28
<212> TYPE: DNA
<213> ORGANISM: Artificial sequence
<220> FEATURE:
<223> OTHER INFORMATION: synthetic oligonucleotide

<400> SEQUENCE: 95
gactgactcc tatagtgagt cgtattac                                           28

<210> SEQ ID NO 96
<211> LENGTH: 32
<212> TYPE: DNA
<213> ORGANISM: Artificial sequence
<220> FEATURE:
<223> OTHER INFORMATION: synthetic oligonucleotide

<400> SEQUENCE: 96
tctgtgtcaa aacctatagt gagtcgtatt ac                                      32

<210> SEQ ID NO 97
<211> LENGTH: 32
<212> TYPE: DNA
<213> ORGANISM: Artificial sequence
<220> FEATURE:
<223> OTHER INFORMATION: synthetic oligonucleotide

<400> SEQUENCE: 97
aaaatgtgtg tgcctatagt gagtcgtatt ac                                      32

<210> SEQ ID NO 98
<211> LENGTH: 32
<212> TYPE: DNA
<213> ORGANISM: Artificial sequence
<220> FEATURE:
<223> OTHER INFORMATION: synthetic oligonucleotide

<400> SEQUENCE: 98
aatgaatgaa tgcctatagt gagtcgtatt ac                                      32

<210> SEQ ID NO 99
<211> LENGTH: 2
<212> TYPE: DNA
<213> ORGANISM: Artificial sequence

```
<220> FEATURE:
<223> OTHER INFORMATION: synthetic oligonucleotide

<400> SEQUENCE: 99 gt                                                                          2

<210> SEQ ID NO 100
<211> LENGTH: 2
<212> TYPE: DNA
<213> ORGANISM: Artificial sequence
<220> FEATURE:
<223> OTHER INFORMATION: synthetic oligonucleotide

<400> SEQUENCE: 100 aa                                                                          2
```

TEMPLATE-DEPENDENT NUCLEIC ACID POLYMERIZATION USING OLIGONUCLEOTIDE TRIPHOSPHATES BUILDING BLOCKS

RELATED APPLICATIONS

This application is a continuation of U.S. patent application Ser. No. 11/211,444 filed on Aug. 25, 2005, which is a divisional of U.S. patent application Ser. No. 10/069,236 filed on Feb. 22, 2002, now U.S. Pat. No. 7,060,440 issued on Jun. 13, 2006, which is a U.S. National Phase of PCT Patent Application No. PCT/IL00/00515 filed on Aug. 29, 2000, which is a continuation of U.S. patent application Ser. No. 09/387,777 filed on Sep. 1, 1999, now abandoned. The contents of all of the above-mentioned applications are incorporated herein by reference.

FIELD AND BACKGROUND OF THE INVENTION

The present invention relates to a novel activity of template-dependent polymerases and, more particularly, to the incorporation of oligonucleotide triphosphates in a template-dependent manner onto a growing nascent oligonucleotide-3'-OH group by such polymerases, to methods exploiting the advantages of the novel activity, to compositions for implementing the methods and to compounds generated while implementing the methods. The present invention provides a novel platform technology, which can be used to develop novel nucleic acid-based applications for biotechnology and nanotechnology including, for example, pharmaceutics, biocatalysis and diagnostics.

It is well recognized that nucleic acid polymers possess functional capacities. These qualities may be exemplified in vivo as specific recognition of tRNA anticodons during translation, and by splicing activity of ribozymes. In vitro, several systems have been established from which functional nucleic acid polymers can be isolated. These methods of in-vitro evolution, termed hereinafter the directed evolution approach, include SELEX (systematic evolution of ligands by exponential enrichment) of RNA (Beaudry & Joyce, 1992) and DNA (Breaker & Joyce, 1994), and iterative use of combinatorial libraries of oligonucleotides (Frank, 1995).

In spite of their poor number of functional groups (i.e., four bases in natural nucleotides), nucleic acid polymers may yield diverse activities such as specific binding affinity to a target molecule or catalysis of chemical-bonds formation. Recently, the inclusion of nucleotide analogs bearing alternative combination of functional groups further extend the vocabulary of nucleic acids, and establish enzymatic approaches for directed evolution as efficient technologies for isolation of functional polymers (Eaton, 1997; Benner et al., 1998; Earnshaw & Gait, 1998).

Naturally-occurring nucleic acid polymers (DNA and RNA) maintain their basic information in the sequence order and combination of four distinct nucleotides, identified by their nitrogenous base moieties adenine and guanine, which are purine derivatives, and cytosine and thymidine (for DNA) or uracil (for RNA), which are pyrimidine derivatives (see FIG. 1).

Information transfer (e.g., DNA-dependent DNA replication, DNA-dependent RNA transcription, RNA-dependent DNA reverse transcription and RNA-dependent RNA replication) is performed enzymatically by mirror copying of the sequence combination in one polymer to a new polymer according to a binary code known as complementation, wherein an adenine nucleotide is complementary to a thymidine nucleotide (or uracil nucleotide) and vice versa, whereas a guanine nucleotide is complementary to a cytosine nucleotide and vice versa.

The genetic binary code, which stores genome information in all organisms over time, entails a simple information transfer key based on electrostatic and steric complementation between two pairs of matching nucleotides. This code has been optimized by natural evolution as advantageous for reliable transfer of genetic information between generations of organisms, between cells within an organism, and between certain complexes and compartments within cells. For example, genetic information is transferred in eukaryotes when DNA stored in the nucleus is transcribed to RNA, which is then translocated to the cytoplasm and translated by the ribosomal machinery to polypeptides.

At the down of evolution, the relatively low complexity of nucleic acid may have been sufficient for the emergence of some activities that were probably limited to assembly and cleavage of nucleic acids. Some of these functions are still exercised today in processes such as splicing and transposition. Later on in evolution, the low complexity of the binary code was mainly utilized for transfer and maintenance of genetic information, while on top of it, a more complex code was developed that dictates synthesis of additional polymers with enhanced complexity—the proteins. These polymers are coded by groups of three successive building blocks of nucleic acids, known as triplet codons, which are recognized and decoded by the ribosomal protein-translation machinery. By evolving the triplet codons, a relatively simple information code in one polymer can be translated and amplified into a new polymer with versatile and wide functional space. The increase in functional capacity may have been a major breakthrough in evolution developments leading to more advanced molecules and organisms.

While conceiving the present invention it was realized that should template-dependent polymerases be able to employ oligonucleotide triphosphates, instead of, or in addition to, nucleotide triphosphates as basic building blocks or units for template-dependent synthesis, the ability to create highly complex polymers having precisely locatable functional groups, and thereby better exploiting the information transfer capacity of nucleic acids in an unprecedented manner exceeding that of nature, will become available.

Assume, for example, the sole use of dinucleotide triphosphates as building blocks for a template-dependent synthesis of a nucleic acid molecule. Sixteen ($2^4$) different dinucleotide triphosphates are available for such synthesis, which represent all of the possible combinations of the four natural nucleotide monomers arranged as dimers. The 16 available dinucleotide triphosphates are: AA-triphosphate (SEQ ID NO:1); AC-triphosphate (SEQ ID NO:2); AG-triphosphate (SEQ ID NO:3); AT-triphosphate (SEQ ID NO:4); CA-triphosphate (SEQ ID NO:5); CC-triphosphate (SEQ ID NO:6); CG-triphosphate (SEQ ID NO:7); CT-triphosphate (SEQ ID NO:8); GA-triphosphate (SEQ ID NO:9); GC-triphosphate (SEQ ID NO:10); GG-triphosphate (SEQ ID NO:1); GT-triphosphate (SEQ ID NO:12); TA-triphosphate (SEQ ID NO:13); TC-triphosphate (SEQ ID NO:14); TG-triphosphate (SEQ ID NO:15); and TT-triphosphate (SEQ ID NO:16).

Further assume that unique functional groups are attached to some or all of the dinucleotide triphosphates building blocks. In this case, a polymer can be synthesized having a maximum of 16 available and precisely locatable types of functional groups, instead of a maximum of only four such groups. It will be appreciated that the maximal number of unique and precisely locatable functional groups depends on the number of monomers employed per oligonucleotide triphosphate. This maximal number equals $4^N$, where N is the number of monomers per oligonucleotide triphosphate.

Therefore, the use of oligonucleotide triphosphates by template-dependent polymerases, instead of, or in addition to, nucleotide triphosphates as basic building blocks or units for template-dependent synthesis, makes possible the creation of highly complex polymers having precisely locatable functional groups.

Furthermore, if the use of oligonucleotides as building blocks for nucleic acid synthesis will become feasible, it will be appreciated that each building block becomes scarcer as compared to the use of nucleotide triphosphates. This phenomenon increases with length (N) of the oligonucleotides employed. Thus, assuming equal representation for each of the four nucleotides in a given nucleic acid polymer, a particular mononucleotide is expected, statistically, every 4 nucleotides in this polymer, a dinucleotide is expected every 16 nucleotides, a trinucleotide every 64 nucleotides (see Table 1, below), a tetranucleotide every 256 nucleotides, a pentanucleotide every 625 nucleotides, and an oligonucleotide of N-mer is expected every $4^N$ nucleotides, in the nucleic acid polymer. Consequently, while using relatively short oligonucleotide sequences as building blocks for template-dependent nucleic acid synthesis, not only the total number of building blocks required for synthesizing a given nucleic acid sequence is reduced, but also each building block is less represented. As is further exemplified below, this feature can be advantageously exploited in detection of nucleic acid sequences and related applications through template-dependent polymerization.

TABLE 1

Nucleotide trimers can be arranged in 64 distinct combinations
(SEQ ID NOs: 17-80, from left to right, top to bottom)

| AAA | AAC | AAG | AAT | ACA | ACC | ACG | ACT | AGA | AGC | AGG | AGT | ATA | ATC | ATG | ATT |
| --- | --- | --- | --- | --- | --- | --- | --- | --- | --- | --- | --- | --- | --- | --- | --- |
| CAA | CAC | CAG | CAT | CCA | CCC | CCG | CCT | CGA | CGC | CGG | CGT | CTA | CTC | CTG | CTT |
| GAA | GAC | GAG | GAT | GCA | GCC | GCG | GCT | GGA | GGC | GGG | GGT | GTA | GTC | GTG | GTT |
| TAA | TAC | TAG | TAT | TCA | TCC | TCG | TCT | TGA | TGC | TGG | TGT | TTA | TTC | TTG | TTT |

Previously, dinucleotides were indicated to be involved in initiation of transcription by RNA polymerase (Shaw et al., 1980), or as building-block units in assembly of oligonucleotide through non-enzymatic means (Leberton et al., 1993; Ordoukhanian & Taylor, 1997; Schmidt et al., 1997). In addition, modified dinucleotides have been used as inhibitors of various viral enzymes such as reverse transcriptase (Jahnke et al., 1995; Jahnke et al., 1997) and integrase (Taktakishvili et al., 2000). However, dinucleotide triphosphates and oligonucleotide triphosphates have not been shown to be involved, to our knowledge, in relation with template-dependent enzymatic polymerization of nucleic acids.

Therefore, there is a widely recognized need for, and it would be highly advantageous to have, methods for better exploiting the information transfer capabilities of nucleic acids (Schmidt et al., 1997; Koppitz et al., 1998; Ogawa et al., 2000), which can serve as a platform technology for development of molecules with novel biological activities, and for the development of novel nucleic acid amplification and identification schemes. Other applications and advantages of these methods will become apparent to those of skills in the art while reading the following sections of the specification.

SUMMARY OF THE INVENTION

One object of the present invention is to develop a new approach to augment both information transfer and functional potential of nucleic acid polymers. According to this novel approach, using oligonucleotide triphosphates as building blocks for template-dependent synthesis of nucleic acids, either per se, or in combination with distinct chemical modifications for the introduction of functional groups in each or some of these oligonucleotides, it is possible to extend the information vocabulary and functional diversity of the polymer in a manner that is correlated to the number (N) of nucleotide units in each oligonucleotide triphosphate.

Another object of the present invention is to develop nucleic acid libraries and functional nucleic acid polymers of unprecedented complexity.

Still another object of the present invention is to develop template-dependent polymerases capable of efficiently exploiting oligonucleotide triphosphates for template-dependent synthesis of nucleic acids.

Yet another object of the present invention is to develop new approaches for template-dependent amplification of nucleic acids.

Yet another object of the present invention is to develop new approaches for nucleic acid-based diagnosis.

Yet another object of the present invention is to develop new approaches for nucleic acid-based chip technology and nanotechnology.

Yet another object of the present invention is to develop new approaches for directed evolution of nucleic acids and polypeptides.

Further and specific objects of the invention include, but are not limited to: (i) the introduction of a novel use of a template-dependent polymerase for incorporating oligonucleotide triphosphates onto a nascent oligonucleotide-3'-OH in a template-dependent manner; (ii) the development of methods for identifying a template-dependent polymerase having increased activity in incorporating oligonucleotide triphosphates onto a nascent oligonucleotide-3'-OH in a template-dependent manner; (iii) the development of methods for assaying a template-dependent polymerase for its activity in incorporating oligonucleotide triphosphates onto a nascent oligonucleotide-3'-OH in a template-dependent manner; (iv) the development of methods for better exploiting the information transfer capacity of nucleic acid molecules; (v) the development of methods for extending a nascent oligonucleotide-3'-OH in a template-dependent manner; (vi) the development of methods for amplifying nucleic acid templates; (vii) the development of methods for exponentially amplifying nucleic acid templates; (viii) the development of methods for detecting a sequence alteration in nucleic acid templates; (ix) the development of methods for detecting the presence or absence of a sequence alteration in nucleic acid templates; (x) the development of methods for determining a sequence of a nucleic acid template; (xi) the development of nucleic acid libraries and functional nucleic acid polymers of unprecedented complexity; (xii) the development of methods for directed evolution of nucleic acids and polypeptides, (xiii) the development of methods for nucleic acid-based chip technology and nanotechnology, and (xiv) the development of compositions for effecting the above methods.

All and any objects of the present invention as stated above are made possible by a novel use of a template-dependent polymerase, the novel use comprising the step of employing the template-dependent polymerase for incorporating at least one oligonucleotide triphosphate onto a nascent oligonucleotide-3'-OH in a template-dependent manner.

According to further features in preferred embodiments of the invention described below, the template-dependent polymerase is selected from the group consisting of DNA-dependent DNA polymerase, DNA-dependent RNA polymerase, RNA-dependent DNA polymerase and RNA-dependent RNA polymerase.

According to still further features in the described preferred embodiments the template-dependent polymerase is thermostable.

According to another aspect of the present invention there is provided a composition or a plurality of compositions comprising $4^N$ oligonucleotide triphosphates each having N monomers, wherein N is an integer greater than 1.

According to still another aspect of the present invention there is provided a composition comprising at least one oligonucleotide triphosphate and at least one nucleotide triphosphate, wherein the at least one oligonucleotide triphosphate and the at least one nucleotide triphosphate are selected such that monomers forming the at least one oligonucleotide triphosphate are not represented among the at least one nucleotide triphosphate and vice versa.

According to further features in preferred embodiments of the invention described below, each of the oligonucleotide triphosphates includes at least two monomers. The number of nucleotide units is preferably up to six, but it may be higher.

According to one preferred embodiment of the invention, the at least one oligonucleotide triphosphate is unmodified with respect to the natural base, sugar, and/or phosphate residues.

According to still further features in the described preferred embodiments, at least one of the oligonucleotide triphosphates is chemically modified in the natural residues of the base, sugar and/or phosphate or any other internucleosidyl linkage.

The present invention successfully addresses the shortcomings of the presently known configurations of nucleic acids as information messengers by exploiting a novel activity of template-dependent polymerases, i.e., their ability to incorporate, in a template-dependent manner, an oligonucleotide triphosphate to a growing 3'-OH group, thereby better exploiting the information transfer capacity of nucleic acids.

BRIEF DESCRIPTION OF THE DRAWINGS

The invention is herein described, by way of example only, with reference to the accompanying drawings, wherein.

Figure 1:
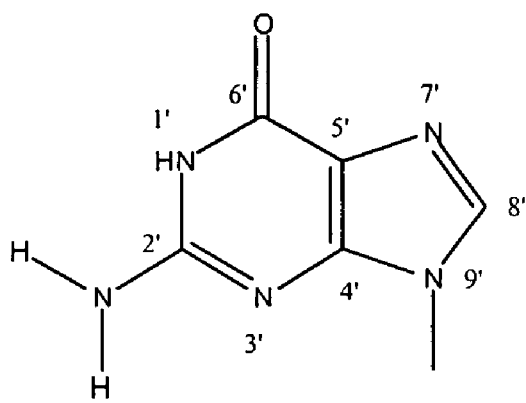
FIG. 1 shows the general formula of the natural 2'-deoxynucleoside wherein Base is one of the four natural bases illustrated in the figure.
Figure 1:
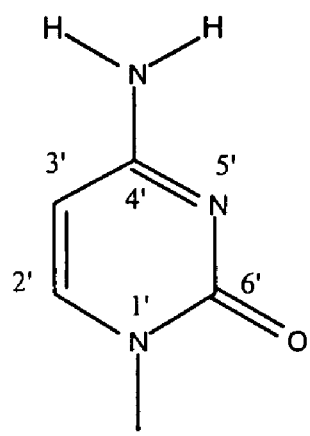
Figure 1:
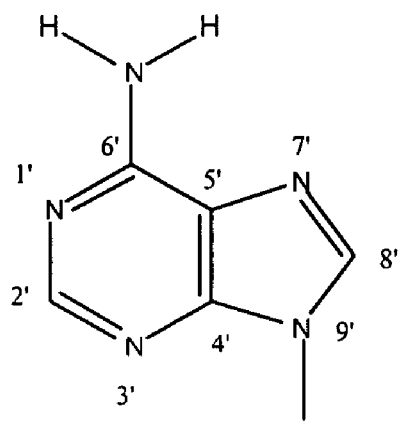
Figure 1:
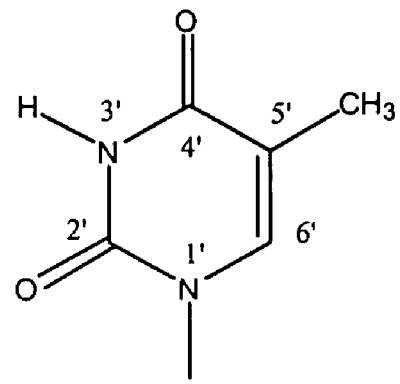
Figure 1:
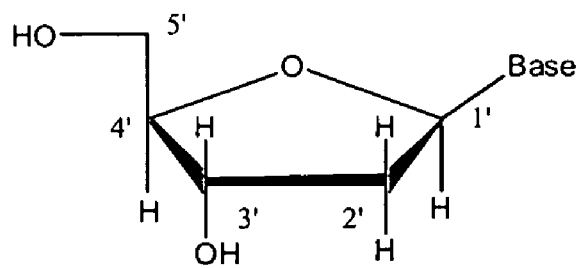

The nucleotide content in these reactions is: all 4 dNTP's (lane 1) and ApG3p and TpC3p dinucleotides (lane 2).

DESCRIPTION OF THE PREFERRED EMBODIMENTS

The present invention is of (i) a novel use of a template-dependent polymerase for incorporating oligonucleotide triphosphates onto a nascent oligonucleotide-3'-OH in a template-dependent manner; (ii) methods for identifying a template-dependent polymerase having increased activity in incorporating oligonucleotide triphosphates onto a nascent oligonucleotide-3'-OH in a template-dependent manner; (iii) methods for assaying a template-dependent polymerase for its activity in incorporating oligonucleotide triphosphates onto a nascent oligonucleotide-3'-OH in a template-dependent manner; (iv) methods for better exploiting the information transfer capacity of a nucleic acid molecule; (v) methods for extending a nascent oligonucleotide-3'-OH in a template-dependent manner; (vi) methods for amplifying a nucleic acid template; (vii) methods for exponentially amplifying a nucleic acid template; (viii) methods for detecting a sequence alteration in a nucleic acid template; (ix) methods for detecting the presence or absence of a sequence alteration in a nucleic acid template; (x) methods for determining a sequence of a nucleic acid template; (xi) nucleic acid libraries and functional nucleic acid polymers of unprecedented complexity and functional space; (xii) methods for directed evolution of nucleic acids and polypeptides; (xiii) methods for nucleic acid-based chip technology and nanotechnology, and (xiv) compositions for effecting the above methods.

The present invention can be used to augment the information transfer capacity and functionality of nucleic acids in a yet unprecedented manner. The present invention can be used as a platform technology for the development of novel nucleic acid-based applications in biotechnology and nanotechnology.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

According to one aspect of the present invention there is provided a novel use of a template-dependent polymerase. The novel use, according to this aspect of the present invention, comprises the step of employing the template-dependent polymerase for incorporating at least one oligonucleotide triphosphate onto a nascent oligonucleotide-3'-OH in a template-dependent manner.

As used herein in the specification and in the claims section that follows, the phrase "template-dependent polymerase" refers to one or more of a structurally diverse group of nucleotidyl-transferase enzymes that catalyze template-dependent extension of nucleic acid polymers, including DNA-dependent DNA polymerases (E.C. 2.7.7.7), DNA-dependent RNA polymerases (E.C. 2.7.7.6), RNA-dependent DNA polymerases (E.C. 2.7.7.49), and RNA-dependent RNA polymerase (E.C. 2.7.7.48). Non-limiting examples of widely employed template-dependent polymerases include T7 DNA polymerase of the phage T7 and T3 DNA polymerase of the phage T3 which are DNA-dependent DNA polymerases, T7 RNA polymerase of the phage T7 and T3 RNA polymerase of the phage T3 which are DNA-dependent RNA polymerases, DNA polymerase I or its fragment known as Klenow fragment of *Escherichia coli* which is a DNA-dependent DNA polymerase, *Thermophilus aquaticus* DNA polymerase, Tth DNA polymerase and vent DNA polymerase, which are thermostable DNA-dependent DNA polymerases, eukaryotic DNA polymerase β, which is a DNA-dependent DNA polymerase, telomerase which is a RNA-dependent DNA polymerase, and non-protein catalytic molecules such as modified RNA (ribozymes; Unrau & Bartel, 1998) and DNA with template-dependent polymerase activity.

Since every living organism contains template-dependent polymerases, the term also refers to such polymerases still awaiting to be uncovered.

In addition, a template-dependent polymerase according to the present invention can be of a natural source, i.e., purified from an organism producing it, or from a recombinant source. Since the genes of the above listed polymerases have been cloned, most of these enzymes are available as recombinant proteins expressed in heterologous expression systems. Yet, it will be appreciated that these genes can be employed to devise methodologies for the isolation of other genes encoding polymerases based on sequence, structural and/or functional similarities or homologies using one or more approaches such as, but not limited to, nucleic acid libraries screening, expression-libraries screening, antibody-based screening, nucleic acid-based hybridization screening, functional screening, polymerase chain-reaction amplification, and the like; the implementation of which for the isolation of desired nucleic acids is well known by the skilled artisan.

As used herein in the specification and in the claims section that follows, the phrases "nascent oligonucleotide-3'-OH" relates to a growing nucleic acid chain having a hydroxyl group at its 3' end. Such a chain may include any number of nucleotides as this term is further defined below. In some cases, even a single nucleotide having a 3'-OH group can serve as an initiator of nascent oligonucleotide-3'-OH. This is particularly true for some RNA-dependent RNA polymerases. Therefore, the term includes nucleic acid chains of at least one nucleotide having a hydroxyl group at its 3' end.

Figure 2:
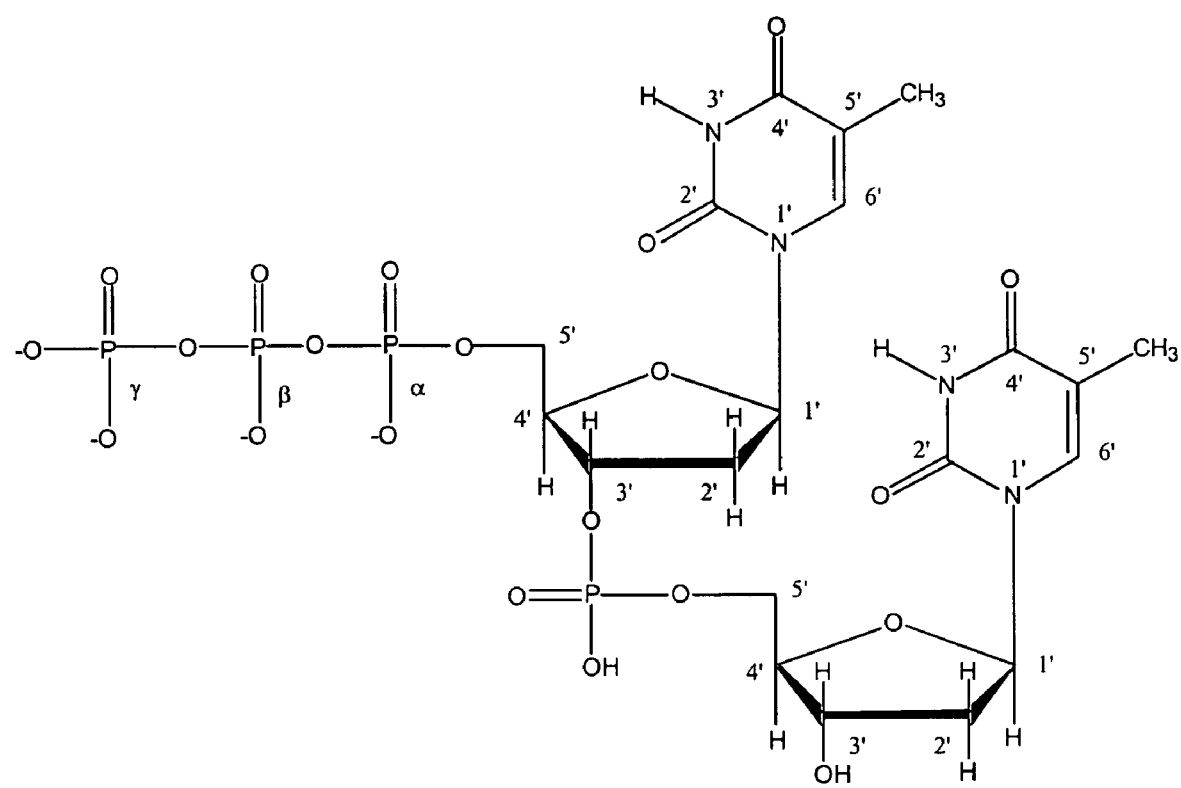
FIG. 2 illustrates the chemical makeup of the thymidylyl-3'-5'-thymidine dinucleotide triphosphate form, TpT3p (SEQ ID NO:16)

As used herein in the specification and in the claims section that follows, the phrases "oligonucleotide triphosphate" or in plural "oligonucleotide triphosphates" include single-stranded chains of at least two nucleotides connected via 3'->5' internucleosidyl linkages, and which have a triphosphate group attached to the 5' end of the first nucleotide as illustrated in FIG. 2.

As used herein in the specification and in the claims section that follows, the terms "nucleotide" or in plural "nucleotides" which are interchangeably used with the terms "monomer" or in plural "monomers" include native (naturally occurring) nucleotides, which include a nitrogenous base selected from the group consisting of adenine, thymidine, cytosine, guanine and uracil, a sugar selected from the group of ribose and deoxyribose (the combination of the base and the sugar is known as nucleoside), and one to three phosphate groups, and which can form phosphodiester internucleosidyl linkages. However, these terms, as used herein, further include nucleotide analogs. Such analogs can have a sugar analog, a base analog and/or an internucleosidyl linkage analog. In addition, analogs exhibiting non-standard base pairing, such as described in, for example, U.S. Pat. No. 5,432,272, which is incorporated herein by reference, is also included under these terms. Thus, as used herein these terms read on molecules capable of, while incorporated in a polymer, conventional or unconventional pairing via hydrogen bonding with naturally occurring nucleotides or with nucleotide analogs exhibiting non standard base pairing and which are present in a complementary polymer.

As used herein in the specifications and in the claims section that follows, the term "nucleotide analog" includes nucleotides that are chemically modified in the natural base (hereinafter "base analogs"), in the natural sugar (hereinafter "sugar analogs"), and/or in the natural phosphodiester or any other internucleosidyl linkage (hereinafter "internucleosidyl linkage analogs").

The nucleotide analogs of the invention may bear at least one functional group selected from: (i) a chemically-reactive group being a group involved in formation or cleavage of any form of a chemical interaction involving electron, proton, or charge transfer including, but not being limited to, a nucleophile, a hydrogen-bond donor, a hydrogen-bond acceptor, an acid, a base, a charged moiety, a hydrophilic moiety, a metal ligand, and a leaving group; (ii) a chemically-inert group being a group involved in interactions that have no electron, proton, or charge transfer, but that may have a structural role, including, but not being limited to, a hydrophobic moiety; (iii) a cross-linking group; (iv) a labeling group, and (v) a first binding-group of a binding pair, which are related to each other by specific binding affinity.

The functional group as above may be linked directly to the base, sugar, or internucleosidyl linkage, or through a spacer, so as to reduce steric hindrance that may interfere with binding to the polymerase and/or with pairing to the template.

It will be appreciated that a variety of functional groups have been successfully bound to nucleotides. It will further be appreciated that such binding did not hamper the ability of template-dependent polymerases to employ nucleotides derivatized by such functional groups as building blocks for template-dependent nucleic acid synthesis.

A first binding group of a binding pair can be any member of a binding pair, such as, but not limited to, biotin-avidin/streptavidin, ligand-receptor, antigen/hapten-antibody, magnetized bead-magnet/electromagnet, substrate analog-enzyme, metal ion-chelator, and the like. The first binding group of the binding pair is preferably selected the smaller one, so as to minimize steric hindrance. In the listed examples, the smaller binding pairs are biotin of the biotin-avidin/streptavidin pair, ligand of the ligand-receptor pair, antigen/hapten of the antigen/hapten (e.g., digoxygenin)-antibody pair, magnetized bead of the magnetized bead-magnet/electromagnet pair, substrate analog of the substrate analog-enzyme pair, and metal ion of the metal ion-chelator pair.

It will be appreciated that a variety of binding groups, such as, but not limited to, biotin, the antigen digoxygenin and magnetized beads have been successfully bound to nucleotides. It will further be appreciated that such binding did not hamper the ability of template-dependent polymerases to employ nucleotides derivatized by binding groups as building blocks for template-dependent synthesis of nucleic acids.

A cross-linking group is a reactive group capable of covalently bonding to another group when appropriate proximity and orientation are established between the groups. A cross-linking group can be selected non-reactive unless activated by an external stimuli, such as radiation of the appropriate wavelength or wavelength range or a chemical. Examples of cross-linking groups which can be bound to a nucleotide include, but are not limited to brominated and iodinated nucleotides such as 5'-bromodeoxyuridine, 8'-bromodeoxyadenosine and 5'-iododeoxycitidine, or thiol-containing nucleotides such as 6'-thiodeoxyguanosine, and 4'-thiodeoxyuridine and additional cross-linking groups as described in Eaton, (1997); Benner et al., (1998); Earnshaw & Gait, (1998) and Sakthivel & Barbas (1998).

It will be appreciated that a variety of cross-linking groups have been successfully bound to nucleotides. It will further be appreciated that such binding did not hamper the ability of template-dependent polymerases to employ nucleotides derivatized by such cross-linking groups as building blocks for template-dependent synthesis of nucleic acids.

A labeling group according to the present invention can be a direct labeling group, i.e., a labeling group which is directly detectable (detectable per se). Examples of direct labeling groups which can be used according to the present invention to label one or more nucleotides of an oligonucleotide triphosphate can be an isotope such as a radioactive isotope, including, but not limited to, $^{14}C$, $^{32}P$, $^{31}P$, $^{2}H$, $^{3}H$, $^{35}S$, $^{125}I$ and the like. The isotope can replace a common isotope participating in the chemical makeup of the nucleotide or, alternatively, the isotope can be added in addition to the atoms constituting the chemical makeup of the nucleotide. A direct labeling group can also be a colorant, e.g., a fluorescent or luminescent group, such as, but not limited to, SPECTRUMORANGE™ (emission at 588 nm), SPECTRUMGREEN™ (538 nm), Aqua (480 nm), Texas-Red (615 nm), and fluorescein-5-iso-thiocyanate (FITC, 525 nm).

A labeling group according to the present invention can alternatively be an indirect labeling group, i.e., a labeling group which is indirectly detectable. It will be appreciated, for example, that any of the above-described binding groups can also serve as an indirect labeling group according to the present invention. In this case, the second binding pair is preferably labeled by a direct labeling group or by an additional indirect labeling group that binds its pair, which is labeled, by a direct labeling group. Alternatively, an indirect labeling group can be an enzyme which directly or indirectly catalyzes a color or chemoluminescent reaction, such as, but not limited to, alkaline phosphatase or peroxidase.

It will be appreciated that a variety of labeling groups has been successfully bound to nucleotides. It will further be appreciated that such binding did not hamper the ability of template-dependent polymerases to employ nucleotides derivatized by such labeling groups as building blocks for template-dependent nucleic acid synthesis.

Examples of base analogs that can be used according to the invention include, but are not limited to, modified purine and pyrimidine bases such as, for example, O-methyl, C-methyl, N-methyl, deaza, aza, halo (F, Br, I), thio, oxo, aminopropenyl, amino, acyl, propynyl, pentynyl, and etheno base derivatives, as well as more drastic modifications such as replacement of the base by phenyl and even complete deletion of the base (abasic), and additional analogs as described in Eaton, (1997); Benner et al., (1998); Earnshaw & Gait, (1998) and Sakthivel & Barbas (1998).

Examples of sugar analogs that can be used according to the invention include, but are not limited to, modifications of the β-ribofuranosyl and β-2'-deoxyribofuranosyl sugar residues such as, for example, 2'-O-methyl, 2'-O-allyl, 2'-O-amino, 2'-deoxy-2'-halo (F, Cl, Br, I), 2'-deoxy-2'-thio, 2'-deoxy-2'-amino and dideoxy derivatives, as well as corresponding α-anomers and hexose analogs, and additional analogs as described in Eaton, (1997); Benner et al., (1998); Earnshaw & Gait, (1998); Groebke et al., (19) and Sakthivel & Barbas (1998).

Examples of internucleosidyl analogs that can be used according to the invention include, but are not limited to, those in which the natural phosphodiester linkage is replaced by a linkage such as phosphorothioate, phosphorodithioate, phosphoroamidate, methylphosphonate, and additional analogs as described in Eaton, (1997); Benner et al., (1998); Earnshaw & Gait, (1998) and Sakthivel & Barbas (1998).

Also can be used peptide nucleic acids (PNA), in which the entire phosphate-sugar backbone is replaced with a backbone consisting of (2-aminoethyl) glycine units to which bases are attached through methylenecarbonyl bridges.

As used herein in the specification and in the claims section that follows, the phrases "template-dependent manner" or "template-dependent synthesis of nucleic acids" refer to successive polymerization of oligonucleotide triphosphates or of oligonucleotide triphosphates and nucleotide triphosphates in a fashion dictated by the sequence order of a complementary template.

In order to better suit the applications proposed herein for the present invention, the polymerization activities of template-dependent polymerases are preferably improved in terms of efficiency and specificity. This can be achieved by modifying certain protein components involved in the catalytic activity of such polymerases.

The rational for engineering polymerase activities is based on available structural and functional information thereof (Joyce and Steitz, 1994; Steitz et al., 1996; Kiefer et al., 1998; Li et al., 1998). The active site of the polymerase provides the specific binding-environment for the substrates including a single-strand template, a complementary primer, divalent metal ions and a matching (complementary) nucleotide triphosphate unit. Specific interactions in the active site are mostly governed by steric and electrostatic factors. As the reaction seems not to go through covalent intermediates, these interactions provide all the physical, chemical and energetic requirements for high fidelity and processive polymerase activity.

The chemistry involves attack of the 5'-α-phosphate of the incoming nucleotide on the 3'-OH group of the end terminal nucleotide of the nascent oligonucleotide, which is deprotonated via the metal ions. This is accompanied by hydrolysis of the triphosphate, release of a pyrophosphate and formation of a phosphodiester bond that extends the primer by one nucleotide at a time.

Polymerase activity further involves major conformational changes of the fingers domain that alternate between "closed" and "open" forms (in the presence and absence of a matching nucleotide triphosphate, respectively), which facilitate alternating between substrate binding, chemical reaction and enzyme sliding along the nucleic acid template.

Protein modifications could conceivably include, but are not limited to, replacements, deletions and insertions of amino acid residues in specific or random locations of the enzyme. As it is presently impractical to anticipate in advance which amino acid modifications will be responsible for functional adjustment, a semi-rational approach for engineering the polymerase is envisioned. Based on the crystal structure available for the large fragment of, for example, Taq DNA polymerase (Li et al., 1998) and other polymerases (Singh & Modak, 1998; Doubli et al., 1999), a set of enzyme domains are chosen for modifications. For example, such domains in Taq DNA polymerase include the O helix of the fingers region (Li et al., 1998; Morales & Kool, 1999). Modifications are introduced into the corresponding gene regions which are cloned in suitable expression vectors by, for example, directed evolution means involving random point-mutations in the chosen domain regions, random shuffling of fragments of part or the whole gene, and family shuffling of genes having similar sequences (Stemmer, 1994; Crameri et al., 1998; Zhao et al., 1998; Minshull & Stemmer, 1999). These generate a library of polymerase genes expressing many different "versions" of the original enzyme, of which individual clones are identified and selected according to specific selection measures.

The main functional goal for polymerase modifications is to improve catalytic efficiency of template-dependent incorporation of oligonucleotide triphosphates. This is the basis for selecting the most proficient enzymes from the diverged library. Proteins expressed from the library are divided into several batches, which are used in a polymerase selection-assay that is further described below. In one step of this assay, the concentration of the appropriate nucleotide units and the reaction time are monitored to select for the best enzyme variants. Chosen clones are further modified by consecutive iterations of the same engineering approach until the desired efficiency is reached.

Thus, it will be appreciated that although template-dependent polymerases are in general tolerant to the use of nucleotide analogs and/or nucleotides derivatized with functional groups, their affinity toward certain analogs and derivatives may be altered. Furthermore, while reducing the present invention to practice, as is exemplified in the Examples section that follows, it was realized that, for example, a certain polymerase has affinity to a certain oligonucleotide triphosphate which is inferior as is compared to its affinity to nucleotide triphosphates in catalyzing the incorporation of these building blocks onto a growing 3'-OH group of a nascent oligonucleotide-3'-OH in a template-dependent manner.

Therefore, according to yet another aspect of the present invention there is provided a method of identifying a template-dependent polymerase having increased activity in incorporating oligonucleotide triphosphates onto a nascent oligonucleotide-3'-OH in a template-dependent manner, the method comprising implementation of the following method steps, of which, in a first step, a library of mutated template-dependent polymerases is constructed.

Such construction can be effected, for example, by mutating (e.g., randomly mutating) a gene encoding the template-dependent polymerase by nucleotide alteration, deletion, addition, shuffling, etc., to obtain a repertoire of mutated template-dependent polymerases genes which encode a repertoire of mutated template-dependent polymerases. Such polymerases can then be expressed by, for example, bacteria or eukaryotic cells, by methods known in the art. In a second step of the method according to this aspect of the present invention, the library, of proteins of individual clones or of pooled clones is screened using template-dependent polymerization of oligonucleotide triphosphates for selecting a template-dependent polymerase mutant exhibiting increased activity in incorporating the oligonucleotide triphosphates onto the nascent oligonucleotide-3'-OH in a template-dependent manner.

An assay for template-dependent polymerization of oligonucleotide triphosphates can be effected in any one of a plurality of ways. The Examples section that follows demonstrate template-dependent polymerization of oligonucleotide triphosphates that can be used with individual or pooled protein extracts, and with purified or partially purified mutant polymerases.

Once a template-dependent polymerase mutant exhibiting increased activity in incorporating oligonucleotide triphosphates onto a nascent oligonucleotide-3'-OH in a template-dependent manner is identified, such a polymerase may serve for a second round of mutating and screening as described above.

Thus, according to a preferred embodiment of this aspect of the present invention, the method is further effected and polished by using the template-dependent polymerase mutant identified above as a basis for creating a second library of mutated template-dependent polymerases derived therefrom and screening the second library using template-dependent polymerization of oligonucleotide triphosphates for selecting a second template-dependent polymerase mutant demonstrating yet increased activity in incorporating the oligonucleotide triphosphates onto the nascent oligonucleotide-3'-OH in a template-dependent manner.

According to still further features in the described preferred embodiments the library of mutated template-dependent polymerases is created using random mutagenesis, random fragments shuffling and/or gene-family shuffling of genes corresponding to protein fragments and/or domains.

According to an additional aspect of the present invention there is provided a method of assaying a template-dependent polymerase for its activity in incorporating oligonucleotide triphosphates onto a nascent oligonucleotide-3'-OH in a template-dependent manner, the method comprising the step of using template-dependent polymerization of oligonucleotide triphosphates for assaying the template-dependent polymerase for its activity in incorporating oligonucleotide triphosphates onto the nascent oligonucleotide-3'-OH in a template-dependent manner.

Oligonucleotide triphosphates may be mixed into compositions, which are useful in implementing the methods of the present invention as are further described below.

Thus, according to another aspect of the present invention there is provided a composition or a plurality of individually packed compositions forming a kit comprising $4^N$ oligonucleotide triphosphates each having N monomers in a single mix or any combination of sub-mixes, wherein N is an integer greater than 1.

Thus, if N equals 2 (dinucleotide), 16 different oligonucleotide triphosphates are included in the single mix or any combination of the sub-mixes; if N equals 3 (trinucleotide), 64 different oligonucleotide triphosphates are included in the single mix or any combination of the sub-mixes; if N equals 4 (tetranucleotide), 256 different oligonucleotide triphosphates are included in the single mix or any combination of the sub-mixes; if N equals 5 (pentanucleotide), 1024 different oligonucleotide triphosphates are included in the single mix or any combination of the sub-mixes; whereas if N equals 6 (hexanucleotide), 4096 different oligonucleotide triphosphates are included in the single mix or any combination of the sub-mixes; and so on.

However, compositions according to the present invention may include oligonucleotide triphosphates and also combinations of oligonucleotide triphosphates and nucleotide triphosphates.

Of particular interest are compositions including at least one oligonucleotide triphosphate and at least one nucleotide triphosphate, wherein the at least one oligonucleotide triphosphate and the at least one nucleotide triphosphate are selected such that monomers forming the at least one oligonucleotide triphosphate are not represented among the at least one nucleotide triphosphate and vice versa. As further detailed below, such compositions may find use in, for example detection of sequence alterations in a nucleic acid template.

Oligonucleotide triphosphates may be attached on a solid support, which are useful in implementing the methods of the present invention as are further described below.

Thus, according to another aspect of the present invention there is provided a setup, in which at least one of the oligonucleotide triphosphates, used for template-dependent polymerization, is attached onto a solid support as part of, for example, a nanodevice or a DNA chip.

The following provides detailed description of some methods, which can find uses in pharmaceutics, biocatalysis, diagnostics, and nanotechnology according to the present invention.

Thus, according to still an additional aspect of the present invention there is provided a method of extending a nascent oligonucleotide-3'-OH in a template-dependent manner, the method comprising the step of contacting the nascent oligonucleotide-3'-OH with a nucleic acid template, a template-dependent polymerase and at least one oligonucleotide triphosphate under conditions in which the nascent oligonucleotide-3'-OH hybridizes with the nucleic acid template and the template-dependent polymerase is active in incorporating the at least one oligonucleotide triphosphate onto a growing 3'-OH group of the nascent oligonucleotide-3'-OH, thereby extending the nascent oligonucleotide-3'-OH in a template-dependent manner.

According to a further aspect of the present invention there is provided still another method of extending a nascent oligonucleotide-3'-OH in a template-dependent manner, the method comprising the step of contacting the nascent oligonucleotide-3'-OH with a nucleic acid template, a template-dependent polymerase and $4^N$ oligonucleotide triphosphates, each including N monomers, wherein N is an integer greater than 1, under conditions in which the nascent oligonucleotide-3'-OH hybridizes with the nucleic acid template and the template-dependent polymerase is active in incorporating said oligonucleotide triphosphates onto a growing 3'-OH group of the nascent oligonucleotide-3'-OH, thereby extending the nascent oligonucleotide-3'-OH in a template-dependent manner.

According to yet a further aspect of the present invention there is provided yet another method of extending a nascent oligonucleotide-3'-OH in a template-dependent manner, the method comprising the step of contacting the nascent oligonucleotide-3'-OH with a nucleic acid template, a template-dependent polymerase, at least one oligonucleotide triphosphate and at least one nucleotide triphosphate, wherein the at least one oligonucleotide triphosphate and the at least one nucleotide triphosphate are selected such that at least one monomer of the at least one oligonucleotide triphosphate is absent from the at least one nucleotide triphosphate, under conditions in which the nascent oligonucleotide-3'-OH hybridizes with the nucleic acid template and the template-dependent polymerase is active in incorporating the at least one oligonucleotide triphosphate and the at least one nucleotide triphosphate onto a growing 3'-OH of the nascent oligonucleotide-3'-OH, thereby extending the nascent oligonucleotide-3'-OH in a template-dependent manner.

According to still a further aspect of the present invention there is provided a method of amplifying a nucleic acid template, the method comprising the step of contacting the nucleic acid template with a nascent oligonucleotide-3'-OH, a template-dependent polymerase and at least one oligonucleotide triphosphate under conditions in which the nascent oligonucleotide-3'-OH hybridizes with the nucleic acid template and the template-dependent polymerase is active in incorporating the at least one oligonucleotide triphosphate onto a growing 3'-OH group of the nascent oligonucleotide-3'-OH, thereby amplifying the nucleic acid template.

According to another aspect of the present invention there is provided another method of amplifying a nucleic acid template, the method comprising the step of contacting the nucleic acid template with a nascent oligonucleotide-3'-OH, a template-dependent polymerase and $4^N$ oligonucleotide triphosphates each including N monomers, wherein N is an integer greater than 1, under conditions in which the nascent oligonucleotide-3'-OH hybridizes with the nucleic acid template and the template-dependent polymerase is active in incorporating the at least one oligonucleotide triphosphate onto a growing 3'-OH group of the nascent oligonucleotide-3'-OH, thereby amplifying the nucleic acid template.

According to still another aspect of the present invention there is provided still another method of amplifying a nucleic acid template, the method comprising the step of contacting the nucleic acid template with a nascent oligonucleotide-3'-OH, a template-dependent polymerase, at least one oligonucleotide triphosphate and at least one nucleotide triphosphate, wherein the at least one oligonucleotide triphosphate and the at least one nucleotide triphosphate are selected such that at least one monomer of the at least one oligonucleotide triphosphate is absent from the at least one nucleotide triphosphate, under conditions in which the nascent oligonucleotide-3'-OH hybridizes with the nucleic acid template and the template-dependent polymerase is active in incorporating the at least one otriphosphate onto a growing 3'-OH group of the nascent oligonucleotide-3'-OH, thereby amplifying the nucleic acid template.

According to an additional aspect of the present invention there is provided a method of exponentially amplifying a nucleic acid template, the method comprising the step of contacting the nucleic acid template with a pair of nascent oligonucleotides-3'-OH, the nascent oligonucleotides-3'-OH being hybridizable with opposite strands of the nucleic acid template, a template-dependent polymerase and $4^N$ oligonucleotide triphosphates each including N monomers, wherein N is an integer greater than 1, under conditions in which the nascent oligonucleotides-3'-OH hybridize with the opposite strands of the nucleic acid template and the template-dependent polymerase is active in incorporating the at least one oligonucleotide triphosphate onto a growing 3'-OH group of each of the nascent oligonucleotides-3'-OH, thereby exponentially amplifying the nucleic acid template.

As further described below, a given gene sequence of interest may be compared to that of a mutant containing one or more base alterations. Using the present invention, a short region near the mutation may be replicated by a polymerase starting from a specific oligonucleotide-3'-OH hybridized thereto. Oligonucleotide triphosphates used for the reaction are doped to fully complement only one of the target sequences, while the oligonucleotide triphosphates that complement the other sequence is omitted from the reaction. The discriminating oligonucleotide triphosphates preferably contain a unique functional group, such as a labeling group as further described above, so as to favor specific recognition of the polymerized products, if any.

Figures 4, 5:
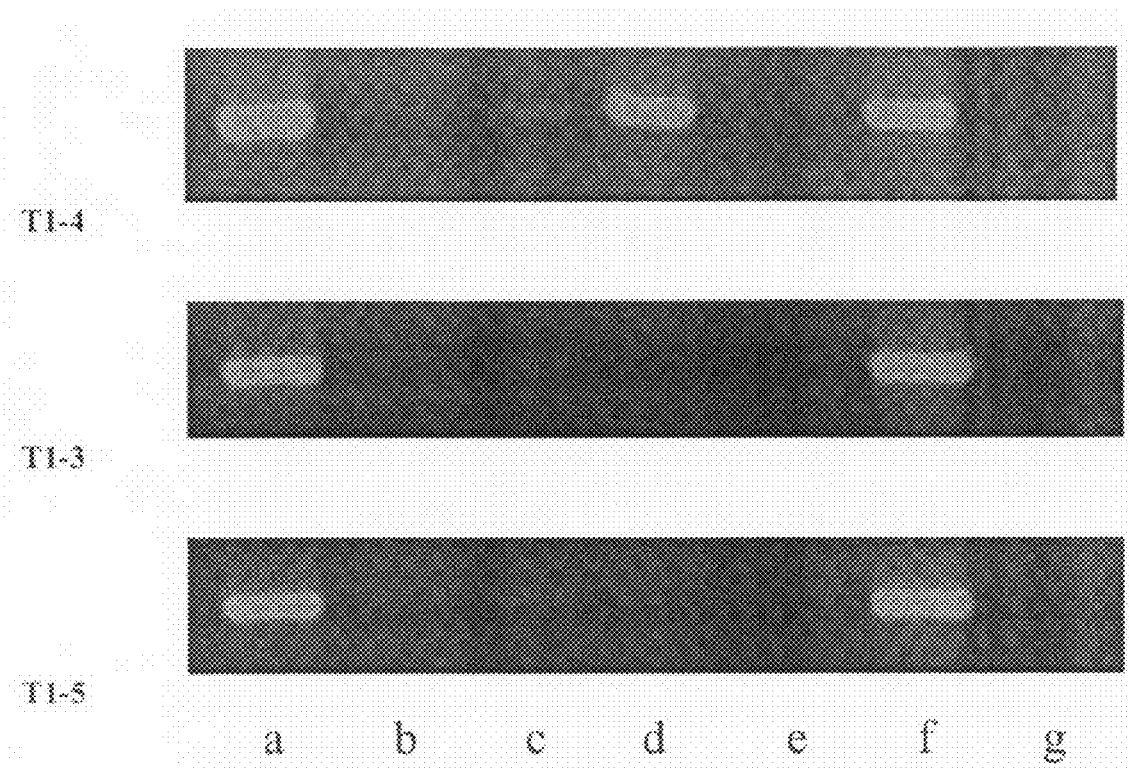
FIG. 4 shows photographs of agarose gels that illustrate the polymerization assay using the templates T14, T1-3 or T1-5 (see Table 2). The reactions in step I (lanes a-e) contained; a: all four dNTP's; b: no dNTP's; c: dATP, dCTP and dGTP; d: as in c, but with 3 µM of TpT3p, e: no T1 template; f-g: PCR of step III with and without T1 template, respectively.
FIG. 5 provides an example of implementing the present invention for distinguishing between gene sequences of a wild type (A, SEQ ID NO:87) and a mutant (B, SEQ ID NO:88) containing a single point mutation (T to G, underlined). The sequences can be replicated from a specific primer at the 5' end (not shown) using the two given sets of dinucleotide combinations and a DNA polymerase. Set I supports complete amplification of A, but not of B due to the presence and absence of the dinucleotides AC and CC, respectively. Accordingly, set II is suitable only for the amplification of sequence B but not of A. The amplified products can be separated from the reaction to indicate which sequence, wild type, mutant or both, are present.

An example of the following concept is illustrated in FIG. 5.

In this case, gene sequences of a wild type (A, SEQ ID NO:87) and a mutant (B, SEQ ID NO:88) containing a single point mutation (T to G, underlined) are analyzed. The sequences can be replicated from a specific primer at the 5' end using the two given sets of dinucleotide combinations and a DNA polymerase. Set I supports complete amplification of A, but not of B due to the presence and absence of the dinucleotides AC and CC, respectively. Accordingly, set II is suitable only for the amplification of sequence B but not of A. The amplified products can be separated from the reaction to indicate which sequence, wild type, mutant or both are present.

Thus, according to yet another aspect of the present invention there is provided a method of detecting a sequence alteration in a nucleic acid template, the method comprising the step of contacting a nascent oligonucleotide-3'-OH with the nucleic acid template, a template-dependent polymerase and at least one oligonucleotide triphosphate under conditions in which the nascent oligonucleotide-3'-OH hybridizes with the nucleic acid template and the template-dependent polymerase is active in incorporating the at least one oligonucleotide triphosphate onto a growing 3'-OH group of the nascent oligonucleotide-3'-OH, thereby extending the nascent oligonucleotide-3'-OH in a template-dependent manner, wherein the at least one oligonucleotide triphosphate is selected so as to enable extending the nascent oligonucleotide-3'-OH in a template-dependent manner only if the sequence alteration is present, or in the alternative, only if the sequence alteration is absent.

According to yet an additional aspect of the present invention there is provided yet an additional method of detecting a sequence alteration in a nucleic acid template, the method comprising the step of contacting the nascent oligonucleotide-3'-OH with a nucleic acid template, a template-dependent polymerase, at least one oligonucleotide triphosphate and at least one nucleotide triphosphate, wherein the at least one oligonucleotide triphosphate and the at least one nucleotide triphosphate are selected such that at least one monomer of the at least one oligonucleotide triphosphate is absent from the at least one nucleotide triphosphate, under conditions in which the nascent oligonucleotide-3'-OH hybridizes with the nucleic acid template and the template-dependent polymerase is active in incorporating the at least one oligonucleotide triphosphate onto the 3'-OH group of the nascent oligonucleotide-3'-OH, thereby extending the nascent oligonucleotide-3'-OH in the template-dependent manner, wherein the at least one oligonucleotide triphosphate is selected so as to enable extending the nascent oligonucleotide-3'-OH in the template-dependent manner only if the sequence alteration is present, or in the alternative, only if the sequence alteration is absent.

According to still an additional aspect of the present invention there is provided still an additional method of detecting the presence or absence of a sequence alteration in a nucleic acid template, the method comprising the steps of: (a) contacting the nucleic acid template with a nascent oligonucleotide-3'-OH, a template-dependent polymerase and at least one oligonucleotide triphosphate under conditions in which the nascent oligonucleotide-3'-OH hybridizes with the nucleic acid template and the template-dependent polymerase is active in incorporating the at least one oligonucleotide triphosphate onto a growing 3'-OH group of the nascent oligonucleotide-3'-OH if appropriate base pairing exists between the nucleic acid template and the oligonucleotide triphosphate, and the template-dependent polymerase is substantially inactive in incorporating the at least one oligonucleotide triphosphate onto the growing 3'-OH group of the nascent oligonucleotide-3'-OH if appropriate base pairing fails to exist between the nucleic acid template and the at least one oligonucleotide triphosphate; and (b) detecting whether the at least one oligonucleotide triphosphate is incorporated onto the growing 3'-OH group of the nascent oligonucleotide-3'-OH, thereby detecting the presence or absence of the sequence alteration in the nucleic acid template.

According to a further aspect of the present invention there is provided a further method of detecting the presence or absence of a sequence alteration in a nucleic acid template, the method comprising the steps of: (a) contacting the nucleic acid template with a nascent oligonucleotide-3'-OH, a template-dependent polymerase, at least one oligonucleotide triphosphate and at least one nucleotide triphosphate, wherein the at least one oligonucleotide triphosphate and the at least one nucleotide triphosphate are selected such that at least one monomer of the at least one oligonucleotide triphosphate is absent from the at least one nucleotide triphosphate, under conditions in which the nascent oligonucleotide-3'-OH hybridizes with the nucleic acid template and the template-dependent polymerase is active in incorporating the at least one oligonucleotide triphosphate and the at least one nucleotide triphosphate onto a growing 3'-OH group of the nascent oligonucleotide-3'-OH if appropriate base pairing exists between the nucleic acid template and the at least one oligonucleotide triphosphate, and the template-dependent polymerase is substantially inactive in incorporating the at least one oligonucleotide triphosphate onto the growing 3'-OH group of the nascent oligonucleotide-3'-OH if appropriate base-pairing fails to exist between the nucleic acid template and the at least one oligonucleotide triphosphate; and (b) detecting whether the oligonucleotide triphosphate is incorporated onto the growing 3'-OH group of the nascent oligonucleotide-3'-OH, thereby detecting the presence or absence of the sequence alteration in the nucleic acid template.

According to yet a further aspect of the present invention there is provided a method of determining a sequence of a nucleic acid template, the method comprising the steps of: (a) contacting in one or more reaction vessels the nucleic acid template with a nascent oligonucleotide-3'-OH, a template-dependent polymerase, $4^N$ oligonucleotide triphosphates each including N monomers, $4^N$ oligonucleotide triphosphate analogs each including N monomers of which a 3' monomer includes a chain-terminator moiety, such as a dideoxy-ribose moiety, wherein N is an integer greater than 1, under conditions in which the nascent oligonucleotide-3'-OH hybridizes with the nucleic acid template and the template-dependent polymerase is active in incorporating the oligonucleotide triphosphates and the oligonucleotide triphosphate analogs onto a growing 3'-OH group of the nascent oligonucleotide-3'-OH, so as to obtain a population of nucleic acid chains each being terminated by a different oligonucleotide triphosphate analog of the $4^N$ oligonucleotide triphosphate analogs; and (b) size-separating, e.g., by gel electrophoresis, the population of terminated nucleic acid chains, thereby determining the sequence of the nucleic acid template.

Several alternative protocols can be followed to execute the above sequencing method, which protocols depend, to a great extent, on the labeling strategy employed.

Thus, if the oligonucleotide-3'-OH is labeled, two options exist. According to the first option, $4^N$ different labels are employed. In this case $4^N$ reaction mixtures are prepared each of which includes a uniquely labeled oligonucleotide-3'-OH and a corresponding unique oligonucleotide triphosphate chain-terminator. Thereafter, a single lane can be employed for electrophoretic separation of the population of nucleic acid chains. According to the second option, a single label is employed. In this case again $4^N$ reaction mixtures are prepared each of which includes the labeled oligonucleotide-3'-OH and a unique oligonucleotide triphosphate chain-terminator. Thereafter, $4^N$ lanes are employed for electrophoretic separation of the population of nucleic acid chains. It will be appreciated that a similar protocol can be adopted if a single label is employed to label the oligonucleotide triphosphates employed in the reaction.

Alternatively, if the oligonucleotide triphosphate terminators are labeled, again, two options exist. According to the first option, $4^N$ different labels are employed. In this case a single reaction mixture is prepared and a single lane can be employed for electrophoretic separation of the population of nucleic acid chains. According to the second option, a single label is employed. In this case again $4^N$ reaction mixtures are prepared and $4^N$ lanes are employed for electrophoretic separation.

Since $4^N$ according to the present invention are at least 16 and further since instrumentation capable of uniquely detecting 16 unique labels is presently not available, according to a preferred embodiment of the present invention at least some of the unique labels are combinatorial labels. Fluorescent combinatorial labels have so far been successfully employed as chromosomal paints to label each of the 24 human male chromosomes by a unique identifiable paint and may therefore serve as unique labels according to the present invention. For further detail regarding combinatorial labels the reader is referred to U.S. Pat. No. 5,871,932, which is incorporated herein by reference.

In any case, the above-described sequencing protocols are advantageous because the number of bands to be read is reduced by a factor of N and resolution is increased as compared to conventional sequencing protocols.

Systems of genetic-information transfer entail accurate transition between two alternate sets of building-block combinations. The information in the new set is then processed by means that are not applicable to the original set. Information systems of DNA and RNA use four natural nucleotides displaying only two mutually exclusive patterns of interactions. Extending the number of information transfer codes in nucleic acid polymers allows better ways to decipher DNA and RNA sequences. The transfer of this information for deciphering and amplification, mostly assisted by enzymes, is a major task in diagnostics and bioinformatics.

The prior art teaches attempts to extend the genetic alphabet with nucleotide analogs presenting alternative pattern of base-pair interactions (Benner, 1995; Lutz et al., 1996; Benner et al., 1998; Kool, 1998; Kool et al, 2000; Ogawa et al., 2000), although these attempts did not provide the requisite specificity for accurate information-transfer applications. Some of these prior art teachings are the subject of U.S. Pat. No. 5,432,272, which is fully incorporated herein by reference.

The present invention presents a novel approach for genetic-information processing based, for example, on the existing set of Watson-Crick recognition-pattern that is stretched out by simply linking two nucleotides in a row. As a result, the coding capacity of nucleic acids is enhanced from 4 to $4^N$ distinct combinations of information transfer units. Deciphering this information in the new polymer may be enhanced by having unique chemical moiety(ies) on each oligomer that can be used to induce specific binding or catalytic activity.

Thus, according to yet an additional aspect of the present invention, there is provided a method of better exploiting the information transfer capacity of a nucleic acid molecule, the method comprising the step of synthesizing a complementary nucleic acid molecule employing oligonucleotide triphosphates instead of, or in addition to, nucleotide triphosphates, as basic units for synthesis.

Directed evolution systems that select for nucleic acid polymers with novel activities can extend their functional repertoire by inclusion of nucleotide analogs with base or sugar modifications (Sakthivel & Barbas, 1998; Tarasow & Eaton, 1998). Permissive modifications of nucleotides are constrained by two main factors: organic chemistry means for synthesis of the nucleotides, and compatibility of the analogs with enzymatic polymerization. Failure to comply with enzymatic polymerization can result from interference of base pairing in the template or of interactions with the polymerase.

Using oligonucleotide triphosphates for polymerization overcome some of the above limitations. The addition of chemical groups in various base and sugar positions may be more suitable for polymerization, as base-pair interactions between the template and the incoming unit are more stable. Unique to this system, the natural connecting phosphodiester-bond between the two nucleosides is now a novel site for modifications extending flexibility and conformational space of the polymeric chain. Furthermore, the complexity of polymers synthesized from $4^N$ different nucleotide building blocks, is much higher than of polymers with a four-base code. For example, a 10-mer oligonucleotide of standard bases has about $10^6$ distinct possibilities, while that of dimers contain about $10^{12}$ different combinations.

In screening for novel lead compounds for drug development, and for polymeric biocatalysts, combinatorial libraries of nucleic acids generated through enzymatic amplification and directed evolution are clearly superior over chemically synthesized libraries. The novel technology of the present invention further strengthens these approaches. The uncovered activity of template-dependent polymerases according to the present invention can serve to generate almost any complex nucleic acid molecule due to the very high complexity of the combinatorial approach.

Thus, it enables the preparation of nucleic acid polymers having at least one functional group in at least one type of nucleotide at a pre-selected location of the polymer.

This aspect of the present invention is readily achievable using functional groups in derivatized oligonucleotide triphosphates. Consider, for example, using dinucleotide triphosphates and a modified A. There are 7 different dimers in which A is in a distinct sequence-context, and therefore one can use up to 7 different functional groups of A when polymerizing with dimers. If trinucleotide triphosphates are used, a modified A can resume any one of 37 distinct trimers (see, for example, all the A-containing trimers in Table 1), and therefore one can use up to 37 different functional groups of A when polymerizing with trimers. If oligonucleotide triphosphates of N monomers are used, a modified A can resume any one of $4^N-3^N$ distinct sequence-context positions and therefore one can use $4^N-3^N$ different functional groups when polymerizing with of N-mer oligonucleotides.

Furthermore, by using a mixture of two different analogs of the same type of nucleotide, the above-described complexity increases to $5^N-3^N$. Therefore, a very large functional diversity can be introduced into a given sequence context of the template by using several different analogs of each nucleotide.

Some of the applications that can be developed based on the new technology are further described in the following paragraphs.

Nucleotide polymers with specific binding affinity or catalytic activity can be isolated from combinatorial libraries of polymers generated using the present invention. The libraries may be initially formed in the DNA sequences through mutations and shuffling by conventional means known to those skilled in the art. The sequence diversity can then be translated to sequence combinations of distinct oligonucleotide building blocks, each containing a unique functional group. The functional polymers are thereafter generated by template-dependent synthesis using a polymerase and can replace proteins in in-vitro applications such as specific nucleases, or create novel catalysts that are useful, for example, in organic synthesis reactions.

Large combinatorial libraries of nucleic acids have been efficiently utilized in screening of lead compounds for developing bioactive compounds such as drugs (Desai et al., 1994; Fauchere et al., 1998). The nucleic acid libraries generated from oligomeric units, according to the present invention, have, potentially, the highest level of complexity, which maximize the diversity and increase the chances of finding a certain bioactive compound, and are therefore more efficient for screening of lead bioactive compounds.

Specific ligands such as oligonucleotides and antibodies are used in chips for recognition and quantitation of DNA and protein molecules. Due to their higher complexity and large repertoire for generating specific ligands, the dinucleotide-based polymers may be used to rival the current molecules in DNA and protein chips.

In nanotechnology, self-assembled units need to form networks that manage information transfer and processing events in molecular scale. Functional nucleic acid polymers embody the basic features for such networks: (a) self-assembly capacity for molecular network setup; (b) addressing-locating an information point in the network by specific recognition and affinity; and (c) information processing-catalytic potential to transfer molecular changes of specific components of the network. The oligonucleotide triphosphate system for nucleic acid polymer synthesis presented herein is the first system to hold all such qualities in one molecule, and is therefore uniquely suited to function as the basis of future "molecular software" in nanotechnology.

Thus, according to yet an additional aspect of the present invention there is provided a method of better exploiting the information transfer and functional capacities of nucleic acid molecules for DNA chip technology and nanotechnology, the method comprising the step of contacting a component selected from at least one nucleic acid template, at least one template-dependent polymerase, at least one nascent oligonucleotide-3'-OH, at least one oligonucleotide triphosphate and/or at least one oligonucleotide triphosphate analog, wherein at least one of said components is attached onto a solid support used in a nanodevice or DNA chip, and wherein said at least one template-dependent polymerase is active in incorporating said at least one oligonucleotide triphosphate and/or said at least one oligonucleotide triphosphate analog onto said growing 3'-OH group of said nascent oligonucleotide-3'-OH, so as to obtain a population of nucleic acid chains bound to the solid support, which can be further manipulated by means as described above including, but not limited to, template-dependent extension, template-dependent amplification, detection of sequence alteration, and detection of nucleic acid sequences.

The directed evolution approach revolutionized the field of nucleic acid and protein engineering. This approach is based on natural evolution strategies that link between multiplication, diversity and fitness. These strategies adopted in the directed evolution approach open enormous possibilities to engineer natural molecules in vitro, and to create de novo unnatural molecules that are useful for mankind (Stemmer, 1994; Zhao et al., 1998; Minshull & Stemmer, 1999). Methods and technologies for performing these tasks are therefore valuable.

Thus, according to yet an additional aspect of the present invention there is provided a method of exploiting oligonucleotide triphosphates for engineering functional nucleic acid polymers and polypeptides by directed evolution, the method comprising the steps of: (a) contacting in reaction vessels a nucleic acid template with a nascent oligonucleotide-3'-OH, a template-dependent polymerase, and $4^N$ oligonucleotide triphosphates, each including N monomers, wherein N is an integer greater than 1, and wherein at least one of said oligonucleotide triphosphates has a mismatch as compared to the template sequence, under conditions in which the nascent oligonucleotide-3'-OH hybridizes with the nucleic acid template and the template-dependent polymerase is active in incorporating said oligonucleotide triphosphates and said at least one oligonucleotide triphosphate containing said mismatch onto a growing 3'-OH group of the nascent oligonucleotide-3'-OH, so as to obtain a population of nucleic acid chains each containing one or multiple mutations; and (b) amplifying said mutated population of nucleic acid chains and further shuffling, cloning and expressing them by methods known in the art to create pools of degenerate nucleic acid sequences and of degenerate polypeptides; and (c) screening said pools for individual clones with desired properties, and then using the selected clones as precursors for additional cycles of degeneration and selection, as described above, until the selected molecules are optimized for the desired function. In this way, the nucleic acid sequences and polypeptides are engineered to acquire specific functional properties.

Additional objects, advantages, and novel features of the present invention will become apparent to one ordinarily skilled in the art upon examination of the following examples, which are not intended to be limiting. Additionally, each of the various embodiments and aspects of the present invention as delineated above and as claimed in the claims section below finds experimental support in the following examples.

EXAMPLES

Reference is now made to the following examples, which together with the above descriptions illustrate the invention in a non-limiting fashion.

Generally, the nomenclature used herein and the laboratory procedures in recombinant DNA technology described below are well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturers' specifications. These techniques and various other techniques are generally performed according to Sambrook et al., (1989), which is incorporated herein by reference. Nucleic acid chemistry is generally performed according to Gait, (1984), which is incorporated herein by reference. All of the oligonucleotides used for the polymerization assays were prepared by solid phase synthesis, and further purified by electrophoresis on Urea-PAGE. Other general references are provided throughout this document. The procedures therein are believed to be well known in the art and are provided for the convenience of the reader. All the information contained therein is incorporated herein by reference.

Example 1

Dinucleotide Triphosphate Preparation

Thymidylyl-3'-5'-thymidine (TpT) dinucleotide was synthesized in liquid by V. Bogachev and V. Silnikove, of the Novosibirsk Institute of Bioorganic Chemistry in Russia. TpT was converted to the triphosphate form (TpT3p, SEQ ID NO:16; FIG. 2) in two steps. First, it was phosphorylated to a 5'-monophosphate form by phosphoryl chloride; then, the 5'-phosphate group was activated by N-methylimidazole and reacted with pyrophosphate (tributylammonium salt) forming the desired triphosphate (Bogachev, 1996).

Following this procedure, 15 mg of TpT-OH (27 mmol) yielded 3 mg (3.8 mmol) of purified TpT3p. The purified dinucleotide was analyzed by $^{31}$P-NMR (D$_2$O) recorded on a Bruker AC 250 spectrometer (Karlsruhe, Germany). $^{31}$P chemical shifts are reported in ppm relative to 80% phosphoric acid and are positive when downfield from the reference. Spectra of four distinct peaks of the triphosphate TpT3p: delta=−10.32 (d, J=19 Hz, P-alpha.), −22.04 (t, J=19 Hz, P-beta.), −7.46 (d, J=19 Hz, P-gamma), and of the phosphodiester phosphate: delta=0.39 (s).

Example 2

Dinucleotide Triphosphate Purification

TpT3p was purified by two ion-exchange chromatography steps: a EMD-DEAE (Merck) column using 0.01-1.2 M LiCl gradient, and by Source 15Q PE column (Pharmacia) using 0.2-1 M NaCl gradient, buffered with 25 mM triethylamine acetate, pH 4. The dinucleotide fractions were further desalted on DEAE Sepharose (Merck) column eluted with 1M triethylamine bicarbonate (TEAB), pH 8. After evaporation and removal of the TEAB, TpT3p was converted to lithium salt by precipitation with a solution of 6% LiClO$_4$ in acetone.

The chromatography conditions in Source 15Q PE column were optimized so that the peak position of TpT3p was clearly distinguished from that of dTTP. The peaks differ by 4 minutes using the above conditions at 1 ml/min, which exclude the possibility that some contamination of dTTP may have been co-purified with the TpT3p and included in the polymerization assay. This result demonstrates the practical availability of highly purified dinucleotide triphosphates.

Paper chromatography (PEI Cellulose F, Merck) of phosphorylated nucleotides was developed with 1M LiCl, and visualized as described (Ludwig, 1981).

Example 3

Polymerization Assay

Methods

Oligonucleotides (Table 2) used for the polymerization assay were purified by electrophoresis on Urea-PAGE. For the polymerization assay, a truncated version of Taq DNA polymerase (543 amino acids of the C-terminus part), was cloned in the pTTQ vector (Stark, 1987), and expressed (in E. coli JM109) and purified as described (Lawyer et al., 1993).

TABLE 2

Oligonucleotides used in the polymerization assay

| Oligo | Sequence (5' to 3') | SEQ ID NO: |
|---|---|---|
| T7 | GTAATACGACTCACTATAGGGC | 81 |
| T1-3 | GGTGTCCTTTGCGTGTCGTGTAAATGCCCTATAGTGAGTCGTATTAC | 82 |
| T1-4 | GGTGTCCTTTGCGTGTCGTGTAAAATGCCCTATAGTGAGTCGTATTAC | 83 |
| T1-5 | GGTGTCCTTTGCGTGTCGTGTAAAAATGCCCTATAGTGAGTCGTATTAC | 84 |
| T2 | GGCCGAAGAGGGTCTCCACGTACCGGTGTCCTTTGCGTGTCGTGT | 85 |
| B | GGCCGAAGAGGGTCTCC | 86 |

Template-extension reaction (step I, FIG. 3) includes a polymerization buffer (40 mM Tricine-KOH, pH 8.0; 16 mM KCl; 3.5 mM MgCl$_2$ and 4 µg BSA), 1 pmol T1 template, 1 pmol T7 primer, 20 nM of each of the four dNTP's and 5 units of DNA polymerase in total volume of 20 µl. Where indicated, 3 µM TpT3p replaced the dTTP in the reaction mix. Reaction was incubated for 2 min at 94° C., 5 minutes at 55° C., 30 seconds at 60° C., 30 seconds at 65° C., and then 10 minutes at 72° C.

Exonuclease-digestion reaction (step II, FIG. 3) included 0.75 units of Exo VII (GibcoBRL), the supplier's buffer and 3 µl of the reaction of step I. Reactions were incubated for 30 minutes at 37° C. and then quenched on ice.

PCR amplification (step III, FIG. 3) included the above described polymerization buffer, additional 2 µg BSA, 1 µl of the reaction of step II, 0.1 mM dNTP's, 0.5 pmol T2 template, and 5 pmol of both, T7 and B primers. The reactions, in 20 µl, were performed in glass capillaries on RapidCycler (Ideho Technology), using thermal steps of: 1 minute at 94° C., followed by 30 cycles of 5 seconds at 94° C., 15 seconds at 50° C.; and 25 seconds at 72° C. The PCR products were separated on 1.4% agarose gels, and visualized by UV light following ethidium bromide staining.

The polymerization assay was also used with Klenow (Exo⁻) DNA polymerase (Fermentas), and Tth DNA polymerase (Promega). Buffer conditions were as recommended by the suppliers. The polymerization assay was performed as described above, but with Klenow step I of the assay differed by incubating the polymerization reaction at 37° C.

Example 4

Polymerization Assay

Results

Figure 3:
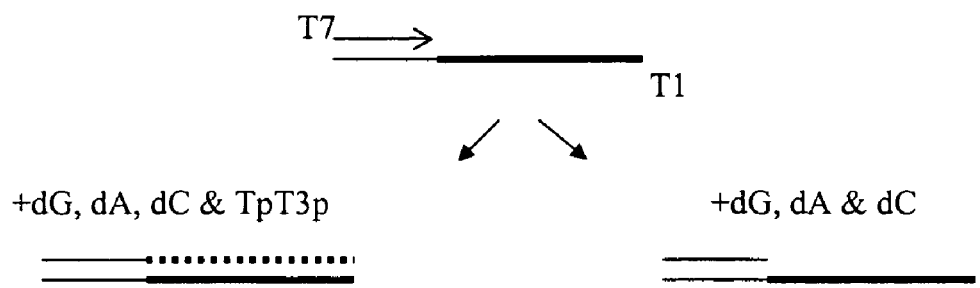
FIG. 3 is a schematic representation of the polymerization assay for detecting incorporation of a dinucleotide triphosphate. Step I: primer extension using primer T7, template T1, DNA polymerase and the deoxynucleotides dATP, dCTP and dGTP in the presence (left) or absence (right) of TpT3P. Step II: treatment of the products from the previous step with Exo VII to eliminate ss-DNA regions. Step III: PCR amplification of the products from the previous step using primers T7 and B, and a connecting fragment, T2, that overlaps with the extended portion of T1 (bold line). This portion of T1 contains a run of 3, 4 or 5 A's (in oligonucleotides T1-3, T1-4 and T1-5, respectively; see Table 2), flanked (on its 5' side) by a non-A containing region. PCR amplification in step III will occur only if the extension proceeded to the end of T1 on step I.
Figure 3:
Figure 3:
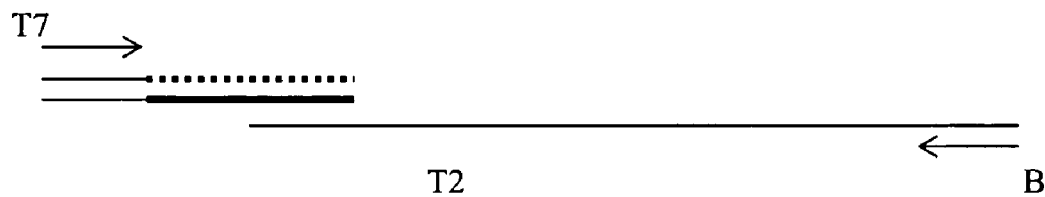

Incorporation of TpT3p by template-dependent polymerization was tested in a very sensitive assay of three steps, as detailed in Example 3 and FIG. 3, and exemplified in FIG. 4. In step 1, a template containing three (T1-3), four (T1-4) or five (T1-5) runs of deoxyadenosine (A), followed by a non-A containing region was extended from a specific oligonucleotide primer (T7) in the presence of a DNA polymerase and the nucleotide mixtures described in Example 3. In step II, the polymerization products were treated by a single-strand specific exonuclease, so that non-extended single-strand regions in T1 were removed. Only products that were extended in step I, but not digested in step II, could be amplified in step III in the presence of oligonucleotides T7, B and T2. This assay is sensitive enough to identify even a small amount of molecules that were extended in step I, and can be used as a general means to amplify the capacity of polymerases to introduce a nucleotide analog by template extension.

The results, shown in FIG. 4, indicate that PCR-amplification products in step III were obtained when the extension in step I included all the templates in the presence of the four dNTP's. When TpT3p replaced dTTP in the dNTP mixture in step I, there were no PCR products with templates T1-3 and T1-5, but only with template T1-4. This demonstrates that DNA polymerase can incorporate the dinucleotide triphosphate TpT3p only when the template contains an even number of A-runs that match the size and base pairing of the thymidine dinucleotide. DNA sequencing of the PCR products of T1-4 extension confirmed the expected sequence of the template.

TpT3p concentration that support primer extension, albeit with lower yield, was found to be 50 nM, which is more than 100 fold higher than that found for dTTP. This suggests affinity differences of the nucleotides to the active site formed by the DNA polymerase, primer and template.

In order to test the possibility that TpT3p inhibits Exo VII in Step II of the polymerization assay, and therefore that the ss-DNA regions for subsequent amplification in step III were retained, an additional experiment performed containing the reactants of step I (but without polymerase added), and 3 µM TpT3p. The absence of any PCR products in both reactions suggests that Exo VII is not inhibited in the presence of 3 µM dinucleotide triphosphates.

These results establish a new concept in enzymatic synthesis of nucleic acids, which opens new avenues for employing polymerases and their substrates in biotechnology.

Example 5

Synthesis and Purification of Additional di- and Trinucleotide Triphosphates

Additional dinucleotide triphosphates and one trinucleotide triphosphate were prepared following essentially the same procedures as described above under Examples 1 and 2. These included the triphosphate form of 2'-deoxycytidylyl (3'-5')-2'-deoxyadenosine (CpA3p, SEQ ID NO:89), 2'-deoxycytidylyl(3'-5')-2'-deoxycytidine (CpC3p, SEQ ID NO:90), 2'-deoxyadenylyl(3'-5')-2'-deoxyguanosine (ApG3p, SEQ ID NO:91), thymidylyl(3'-5')-2'-deoxycytidine (TpC3p, SEQ ID NO:14) and thymidylyl-3'-5'-thymidylyl-3'-5'-thymidine (TpTpT3p, SEQ ID NO:80). These compounds were all analyzed by $^{31}$P-NMR giving the expected peak spectra corresponding to the four phosphate groups.

The oligonucleotide triphosphates were purified essentially as described under Example 2 above using a Source 15Q PE column (Pharmacia) and a gradient of 0-40% ethanol buffered with 50 mM triethylamine bicarbonate (TEAB), pH 7.5-8.0, at flow rate of 1.6 ml/minute (see Table 3 below). The chromatography conditions were optimized to distinguish between the dinucleotides and their corresponding mono-dNTP's so as to eliminate even traces thereof from the preparations.

TABLE 3

HPLC purification of dinucleotide triphosphates

| Nucleotides | Peak position in HPLC (minutes) | Peak absorbance (nm*) |
| --- | --- | --- |
| dATP | 27.8 | 261 |
| dCTP | 22.5 | 271 |
| dGTP | 25.2 | 253 |
| TTP | 24.3 | 266 |
| TpT3p | 28 | 266 |
| TpTpT3p | 32 | 266 |
| CpA3p | 28.9 | 263 |
| TpC3p | 25.7 | 268 |
| ApG3p | 28.5 | 255 |

*absorbance was measured during the HPLC run in the TEAB/ethanol buffer

Example 6

Labeled-Primer Extension Assay

Methods

The oligonucleotides that were used for this assay are detailed in Table 4 before. The reactions of labeled-primer extension included: polymerization buffer (40 mM Tricine-KOH, pH 8.0; 16 mM KCl; 5 mM MgCl$_2$ and 4 µg BSA), 1 pmol template, 0.2 pmol of the p201 primer (labeled at its 5' with P 32-γ-ATP using T4 polynucleotide kinase), 1 μM of the indicated dNTP's and 50 μM of the indicated di- or trinucleotide triphosphates in a total volume of 20 μl. The reactions were incubated for 5 minutes at 45° C., then 5 units of Taq DNA polymerase (see Example 3 for details) were added, followed by 20 minutes at 72° C. The reactions were terminated with 15 μl of stop solution (95% formamide, 20 mM EDTA and 0.05% bromophenol blue). Three μl were then separated on Urea-PAGE, and the radiolabeled DNA-bands were detected by phosphoimaging.

TABLE 4

Oligonucleotides used in the labeled-primer extension assay

| Oligo | Sequence (5' to 3') | SEQ ID NO: |
|---|---|---|
| P201 | GTAATACGACTCACTATAGG | 92 |
| T80 | AAAATGTGTGTGCCTATAGTGAGTCGTATTAC | 93 |
| T81 | AATGAATGAATGCCTATAGTGAGTCGTATTAC | 94 |
| T83 | GACTGACTCCTATAGTGAGTCGTATTAC | 95 |
| T24 | TCTGTGTCAAAACCTATAGTGAGTCGTATTAC | 96 |

Example 7

Labeled-Primer Extension Assay

Results

Figure 6:
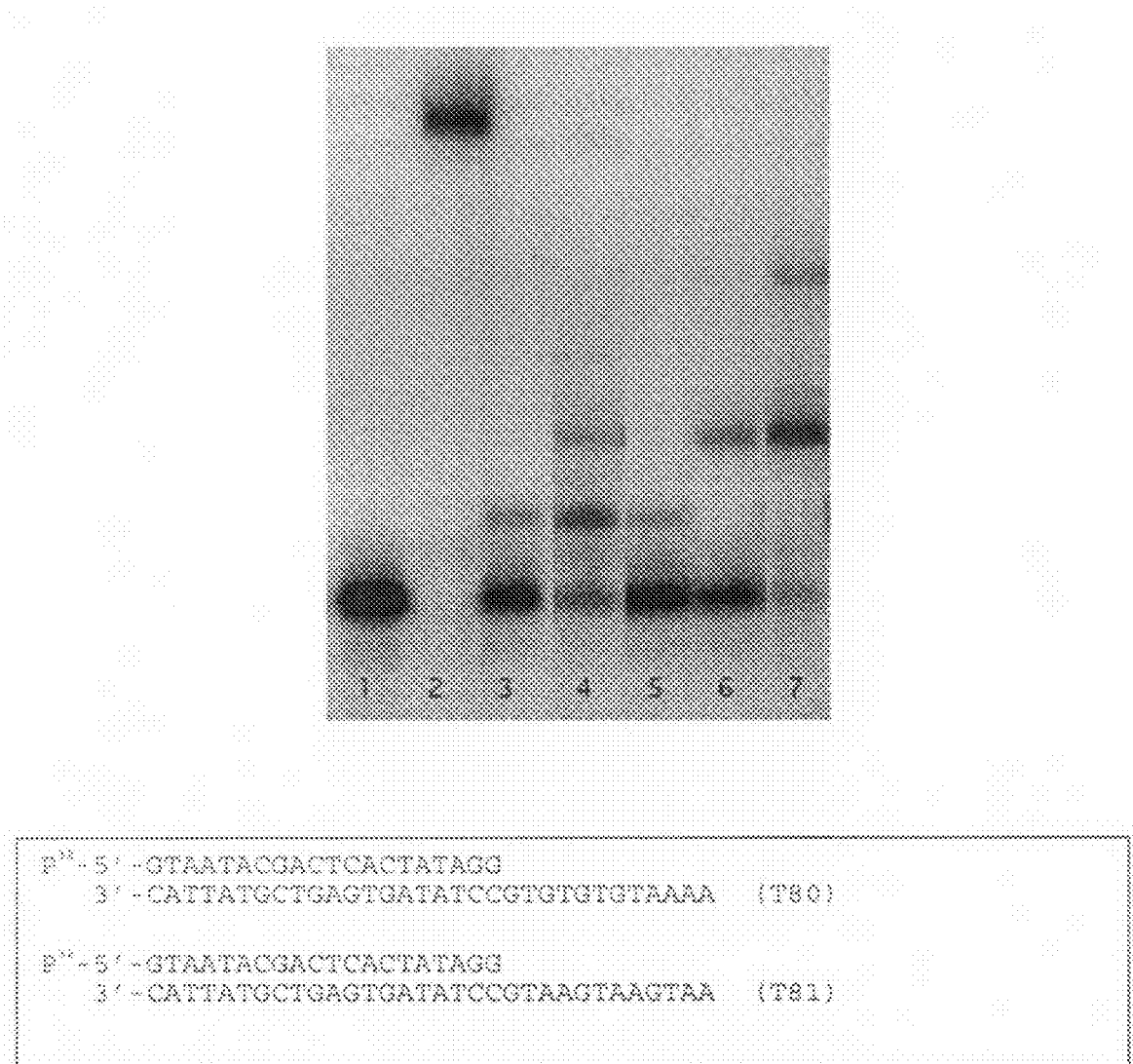
FIG. 6 shows an assay of labeled-primer extension demonstrating incorporation of the dinucleotide triphosphates TpT3p and CpA3p in a template-dependent manner onto a 3' end of a primer. The reactions includes labeled primer p201 (SEQ ID NO:92) and templates T80 (SEQ ID NO:93) (lanes 1-4), and T81 (SEQ ID NO:94) (lanes 5-7). The nucleotides content in these reactions is: none (lane 1), all 4 dNTP's (lane 2), CpA3p (lanes 3 and 5), CpA3p and TpT3p (lanes 4, 6 and 7). The reaction in lane 7 contains two fold the concentration of dinucleotides as is compared to that of lane 6.
Figure 7:
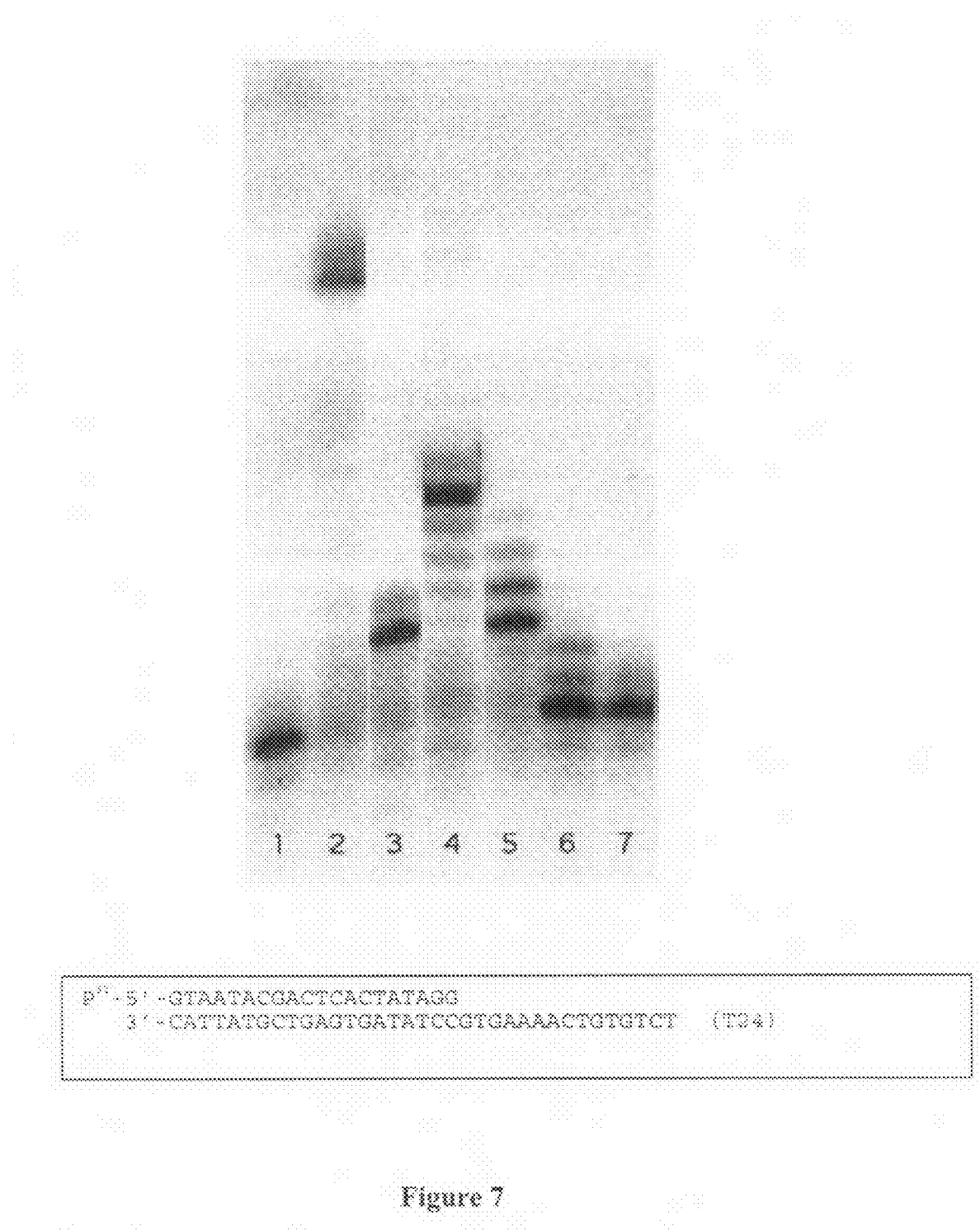
FIG. 7 shows an assay of labeled-primer extension demonstrating incorporation of di- and trinucleotide triphosphates in a template-dependent manner onto a 3' end of a primer. The reactions include labeled primer p201 (SEQ ID NO:92) and template T24 (SEQ ID NO:96). The nucleotide content in these reactions is: none (lane 1), all 4 dNTP's (lane 2), dCTP and dATP (lane 3), dCTP, dATP and TpT3p (lane 4), dCTP, dATP and TpTpT3p (lane 5), CpA3p (lane 6), and CpC3p (lane 7)
Figure 8:
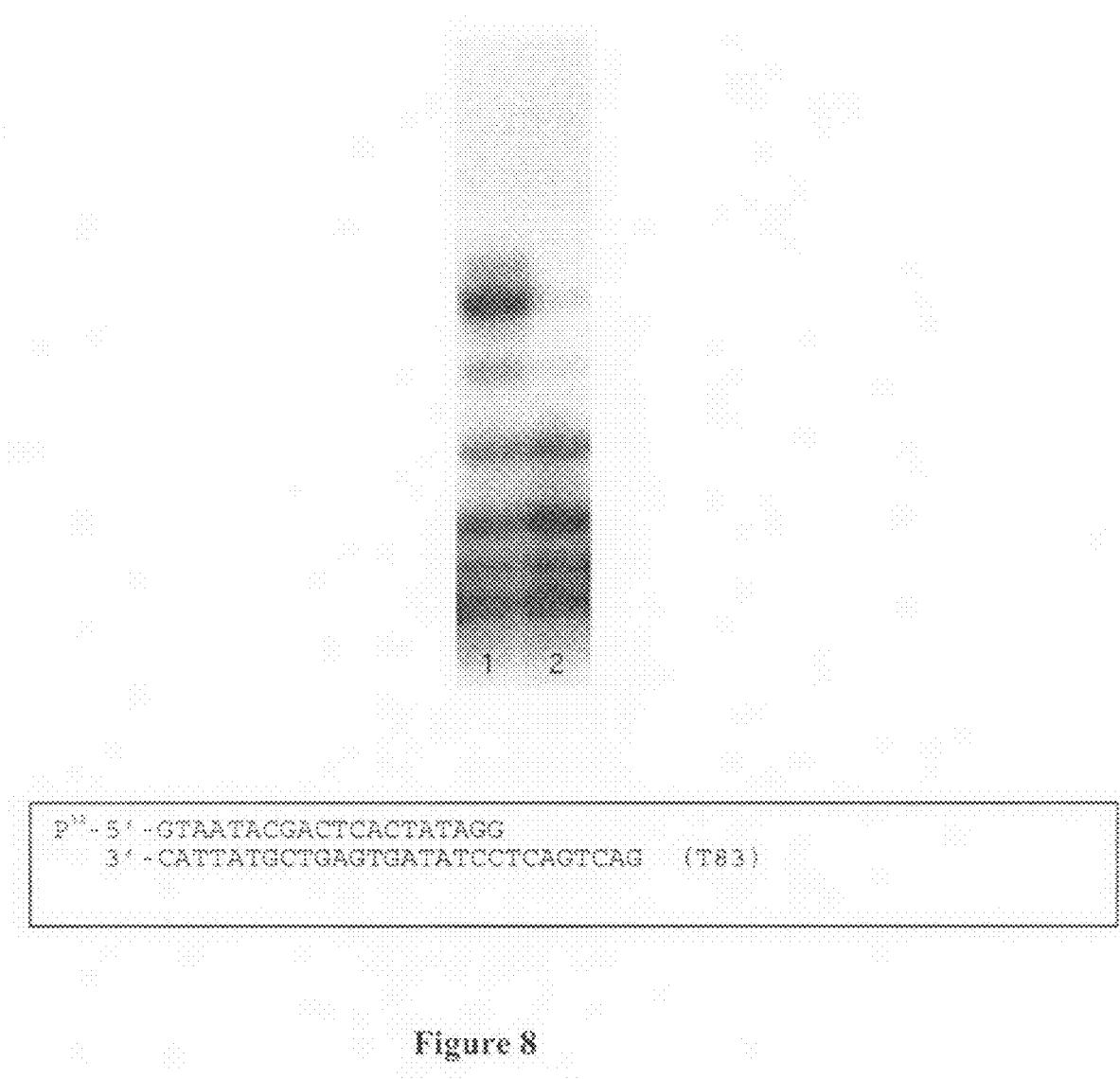
FIG. 8 shows an assay of labeled-primer extension demonstrating template-dependent incorporation of ApG3p and TpC3p dinucleotides. The reactions include labeled primer p201 (SEQ ID NO:92) and template T83 (SEQ ID NO:95).

In addition to the above described results (Example 4), incorporation of a variety of dinucleotides by template-dependent polymerization was analyzed using a labeled-primer extension assay, which enabled to clearly visualize and follow the polymerization products (FIGS. 6, 7 and 8). Templates T80 (SEQ ID NO:97) and T81 (SEQ ID NO:98) were designed to have combinations of GT (SEQ ID NO:99) and AA (SEQ ID NO:100) bases for primer extension, which allow to investigate template-dependent incorporation of the complementary dinucleotides CpA3p and TpT3p, respectively. The results in FIG. 6 demonstrate correct incorporation of both dinucleotide triphosphates CpA3p and TpT3p (FIG. 6, lanes 3-7), albeit with a lower efficiency as compared to the incorporation of the natural dNTP's (FIG. 6, lane 2). The experiment of FIG. 7 shows temple-dependent incorporation of a mix between a subset of two mononucleotides (dCTP and dATP), and TpT3p (FIG. 7, lane 4), or with TpTpT3p (FIG. 7, lane 5). In both cases the unnatural building blocks are utilized, but the dinucleotide is incorporated much better than the trinucleotide. In both cases, however, there are traces in the background of polymerization halts in the size of single nucleotides. This seems to be a result of esterase activity of polymerases that is well documented (Canard et al., 1995; Meyer et al., 1998). Incorporation of the dinucleotides CpA3p and CpC3p is compared in FIG. 7 (lanes 6 and 7, respectively). Only the complementary dinucleotide (CpA3p) seems to be incorporated by the polymerase, indicating a correct template-dependent synthesis. In FIG. 8, two additional dinucleotides, ApC3p and TpC3p, are analyzed for specific incorporation using the template T83 (SEQ ID NO:95). Altogether, four distinct dinucleotide triphosphates and a single trinucleotide triphosphates have been shown to be incorporated in a template-dependent manner by DNA polymerase, demonstrating a new means to synthesize nucleic acid polymers.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES

1. Beaudry, A. A., and Joyce, G. F. (1992). Directed evolution of an RNA enzyme. Science 257, 635-641.
2. Benner, S. A. (1995). Method for incorporation into a DNA or RNA oligonucleotide using nucleotide bearing heterocyclic bases. U.S. Pat. No. 5,432,272
3. Benner, S. A., Battersby, T. R., Eschgfaller, B., Hutter, D., Kodra, J. T., Lutz, S., Arslan, T., Baschlin, D. K., Blattler, M., Egli, M., Hammer, C., Held, H. A., Horlacher, J., Huang, Z., Hyrup, B., Jenny, T. F., Jurczyk, S. C., Konig, M., von, K. U., Lutz, M. J., MacPherson, L. J., Moroney, S. E., Muller, E., Nambiar, K. P., Piccirilli, J. A., Switzer, C. Y., Vogel, J. J., Richert, C., Roughton, A. L., Schmidt, J., Schneider, K. C., and Stackhouse, J. (1998). Redesigning nucleic acids. Pure Appl Chem 70, 263-266.
4. Bogachev, V. S. (1996). Synthesis of Deoxynu5'-Triphosphate using trifluoroacetic anhydride as an activating reagent. Bioorg Khim 22, 699-705.
5. Breaker, R. R., and Joyce, G. F. (1994). Inventing and improving ribozyme function: rational design versus iterative selection methods. Proc Natl Acad Sci, USA 12, 268-275.
6. Canard, B., Cardona, B., and Sarfati, R. S. (1995). Catalytic editing properties of DNA polymerases. Proc Natl Acad Sci USA, 92, 10859-10863.
7. Crameri, A., Raillard, S. A., Bermudez, E., and Stemmer, W. P. (1998). DNA shuffling of a family of genes from diverse species accelerates directed evolution. Nature 391, 288-291.
8. Desai, M. C., Zuckermann, R. N., and Moos, W. H. (1994). Recent Advances in the Generation of Chemical Diversity Libraries. Drug Dev Res 33, 174-188.
9. Doubli?, S., Sawaya, M. R., and Ellenberger, T. (1999). An open and closed case for all polymerases. Structure 7, 31-35.
10. Earnshaw, D. J., and Gait, M. J. (1998). Modified oligoribonucleotides as site-specific probes of RNA structure and function. Biopolymers 48, 39-55.
11. Eaton, B. E. (1997). The joys of in vitro selection: chemically dressing oligonucleotides to satiate protein targets. Curr Opin Chem Biol 1, 10-16.
12. Fauchere, J. L., Boutin, J. A., Henlin, J. M., Kucharczyk, N., and Ortuno, J. C. (1998). Combinatorial chemistry for the generation of molecular diversity and the discovery of bioactive leads. Chemometr Intel Lab Sys 43, 43-68.

13. Frank, R. (1995). Simultaneous and combinatorial chemical synthesis techniques for the generation and screening of molecular diversity. J Biotechnol 41, 259-272.
14. Gait, M. J. (1984). Oligonucleotide synthesis: a practical approach IRL press, Oxford, England
15. Groebke, K., Hunziker, J., Fraser, W., Peng, L., Diederichsen, U., Zimmermann, K., Holzner, A., Leumann, C., and Eschenmoser, A. (1998). Why pentose- and not hexose-nucleic acids? Purine-purine pairing in homo-DNA: Guanine, isoguanine, 2,6-diaminopurine, and xanthine. Hel Chim Acta 81, 375-474.
16. Jahnke, T. S., and Nair, V. (1995). 2'-Deoxyadenylyl-(3'-] 5')-Isodideoxyadenosine, a Unique Dinucleotide—Synthesis, Enzymology, and Conformational Studies. Bioorg Med Chem Lett 5, 2235-2238.
17. Jahnke, T. S., Chao, Q., and Nair, V. (1997). Dinucleotides incorporating isomeric nucleosides: Synthesis, structural and stereochemical characterization, and enzymology. Nucleosides & Nucleotides 16, 1087-1090.
18. Joyce, C. M., and Steitz, T. A. (1994). Function and structure relationships in DNA polymerases. Annu Rev Biochem 63, 777-822.
19. Kiefer, J. R., Mao, C., Braman†, J. C., and Beese, L. S. (1998). Visualizing DNA replication in a catalytically active *Bacillus* DNA polymerase crystal. Nature 391, 304-307.
20. Kool, E. T. (1998). Replication of non-hydrogen bonded bases by DNA polymerases: A mechanism for steric matching. Biopolymers 48, 3-17.
21. Kool, E. T., Morales, J. C., and Guckian, K. M. (2000). Mimicking the structure and function of DNA: Insights into DNA stability and replication. Angew. Chem.-Int. Ed. 39, 991-1009.
22. Koppitz, M., Nielsen, P. E., and Orgel, L. E. (1998). Formation of oligonucleotide-PNA-chimeras by template-directed ligation. J Am Chem Soc 120, 4563-4569.
23. Lawyer, F. C., Stoffel, S., Saiki, R. K., Chang, S. Y., Landre, P. A., Abramson, R. D., and Gelfand, D. H. (1993). High-level expression, purification, and enzymatic characterization of full-length *Thermus aquaticus* DNA polymerase and a truncated form deficient in 5' to 3' exonuclease activity. PCR Methods Appl 2, 275-287.
24. Leberton, J., De, M. A., Waldner, A., Fritch, V., Wolf, R. M., and Freier, S. M. (1993). Synthesis of thymidine dimer derivatives containing an amide linkage and their incorporation into oligodeoxynucleotides. Tetrahedron Lett 34, 6383-6386.
25. Li, Y., Korolev, S., and Waksman, G. (1998). Crystal structures of open and closed forms of binary and ternary complexes of the large fragment of *Thermus aquaticus* DNA polymerase I: structural basis for nucleotide incorporation. EMBO J. 17, 7514-7525.
26. Ludwig, J. (1981). A new route to nucleoside 5'-triphosphates. Acta Biochim Biophys Acad Sci Hung 16, 131-133.
27. Lutz, M. J., Held, H. A., Hottiger, M., Hubscher, U., and Benner, S. A. (1996). Differential discrimination of DNA polymerase for variants of the non-standard nucleobase pair between xanthosine and 2,4-diaminopyrimidine, two components of an expanded genetic alphabet. Nucleic Acids Res 24, 1308-1313.
28. Meyer, P. R., Matsuura, S. E., So, R. G., and Scott, W. A. (1998). Unblocking of chain-terminated primer by HIV-1 reverse transcriptase through a nucleotide-dependent mechanism. Proc. Natl. Acad. Sci. USA, 95, 13471-13476.
29. Minshull, J., and Stemmer, W. P. (1999). Protein evolution by molecular breeding. Curr Opin Chem Biol 3, 284-290.
30. Morales, J. C., and Kool, E. T. (1999). Minor groove interactions between polymerase and DNA: More essential to replication than Watson-Crick hydrogen bonds? J Am Chem Soc 121, 2323-2324.
31. Ogawa, A. K., Wu, Y. Q., McMinn, D. L., Liu, J. Q., Schultz, P. G., and Romesberg, F. E. (2000). Efforts toward the expansion of the genetic alphabet: Information storage and replication with unnatural hydrophobic base pairs. J. Am. Chem. Soc., 122, 3274-3287.
32. Ordoukhanian, P., and Taylor, J. S. (1997). Solid phase-supported thymine dimers for the construction of dimer-containing DNA by combined chemical and enzymatic synthesis: a potentially general method for the efficient incorporation of modified nucleotides into DNA. Nucleic Acids Res 25, 3783-3786.
33. Sakthivel, K., and Barbas, C. F. (1998). Expanding the potential of DNA for binding and catalysis: Highly functionalized dUTP derivatives that are substrates for thermostable DNA polymerases. Angew Chem Int Ed Engl 37, 2872-2875.
34. Sambrook, J., Fritsch, E. F., and Maniatis, T. (1989). Molecular cloning—a laboratory manual Cold Spring Harbor Laboratory Press, Cold Spring Harbor, N.Y.
35. Schmidt, J. G., Christensen, L., Nielsen, P. E., and Orgel, L. E. (1997). Information transfer from DNA to peptide nucleic acids by template-directed syntheses. Nucleic Acids Res 25, 4792-4796.
36. Shaw, P. A., Marshall, M. V., and Saunders, G. F. (1980). Dinucleotide priming of RNA synthesis. Cytogenet Cell Genet 26, 211-222.
37. Singh, K., and Modak, M. J. (1998). A unified DNA- and dNTP-binding mode for DNA polymerases. Trends Biochem Sci 23, 277-281.
38. Stark, M. J. (1987). Multicopy expression vectors carrying the lac repressor gene for regulated high-level expression of genes in *Escherichia coli*. Gene 51, 255-267.
39. Steitz, T. A., Wang, J., Eom, S. H., Jaeger, J., Restle, T., and Jeruzalmi, D. (1996). DNA and RNA polymerases: Structural diversity and common mechanisms. FASEB J 10, 795-795.
40. Stemmer, W. P. (1994). DNA shuffling by random fragmentation and reassembly: in vitro recombination for molecular evolution. Proc Natl Acad Sci, USA 91, 10747-10751.
41. Taktakishvili, M., Neamati, N., Pommier, Y., Pal, S., and Nair, V. (2000). Recognition and inhibition of HIV integrase by novel dinucleotides. J Am Chem Soc 122, 5671-5677.
42. Tarasow, T. M., and Eaton, B. E. (1998). Dressed for success: Realizing the catalytic potential of RNA. Biopolymers 48, 29-37.
43. Unrau, P. J., and Bartel, D. P. (1998). RNA-catalysed nucleotide synthesis. Nature 395, 260-263.
44. Zhao, H., Giver, L., Shao, Z., Affholter, J. A., and Arnold, F. H. (1998). Molecular evolution by staggered extension process (StEP) in vitro recombination. Nat Biotechnol 16, 258-261.

What is claimed is:

1. A method of amplifying a nucleic acid template, the method comprising the step of contacting the nucleic acid template with a nascent oligonucleotide-3'-OH, a template-dependent polymerase and at least one oligonucleotide triphosphate under conditions in which said nascent oligonucleotide-3'-OH hybridizes with the nucleic acid template and said template-dependent polymerase is active in incorporating said at least one oligonucleotide triphosphate onto a growing 3'-OH group of said nascent oligonucleotide-3'-OH, thereby amplifying the nucleic acid template, wherein said template-dependent polymerase is a DNA polymerase.

2. A method of amplifying a nucleic acid template, the method comprising the step of contacting the nucleic acid template with a nascent oligonucleotide-3'-OH, a template-dependent polymerase and $4^N$ oligonucleotide triphosphates each including N monomers, wherein N is an integer equal to 2 or 3, under conditions in which said nascent oligonucleotide-3'-OH hybridizes with the nucleic acid template and said template-dependent polymerase is active in incorporating said at least one oligonucleotide triphosphate onto a growing 3'-OH group of said nascent oligonucleotide-3'-OH, thereby amplifying the nucleic acid template.

3. A method of exponentially amplifying a nucleic acid template, the method comprising the step of contacting the nucleic acid template with a pair of nascent oligonucleotides-3'-OH, said nascent oligonucleotides-3'-OH being hybridizable with opposite strands of the nucleic acid template, a template-dependent polymerase and $4^N$ oligonucleotide triphosphates each including N monomers, wherein N is an integer equal to 2 or 3, under conditions in which said nascent oligonucleotides-3'-OH hybridize with said opposite strands of the nucleic acid template and said template-dependent polymerase is active in incorporating said at least one oligonucleotide triphosphate onto a growing 3'-OH group of each of said nascent oligonucleotides-3'-OH, thereby exponentially amplifying the nucleic acid template.

4. A method of amplifying a nucleic acid template, the method comprising the step of contacting the nucleic acid template with a nascent oligonucleotide-3'-OH, a template-dependent polymerase, at least one oligonucleotide triphosphate and at least one nucleotide triphosphate, wherein said at least one oligonucleotide triphosphate and said at least one nucleotide triphosphate are selected such that at least one monomer of said at least one oligonucleotide triphosphate is absent from said at least one nucleotide triphosphate, under conditions in which said nascent oligonucleotide-3'-OH hybridizes with the nucleic acid template and said template-dependent polymerase is active in incorporating said at least one oligonucleotide triphosphate onto a growing 3'-OH group of said nascent oligonucleotide-3'-OH, thereby amplifying the nucleic acid template, wherein said template-dependent polymerase is a DNA polymerase.

* * * * *